(12) United States Patent
Matsui et al.

(10) Patent No.: US 11,927,531 B2
(45) Date of Patent: Mar. 12, 2024

(54) INFORMATION PROCESSING DEVICE, STORAGE CONTAINER, AND NON-TRANSITORY COMPUTER READABLE MEDIUM

(71) Applicant: DAIKIN INDUSTRIES, LTD., Osaka (JP)

(72) Inventors: Hidenori Matsui, Osaka (JP); Kiichirou Satou, Osaka (JP); Shouichi Tanno, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 17/915,974

(22) PCT Filed: Mar. 31, 2021

(86) PCT No.: PCT/JP2021/014068
§ 371 (c)(1),
(2) Date: Sep. 29, 2022

(87) PCT Pub. No.: WO2021/201184
PCT Pub. Date: Oct. 7, 2021

(65) Prior Publication Data
US 2023/0117594 A1     Apr. 20, 2023

(30) Foreign Application Priority Data
Mar. 31, 2020   (JP) .................. 2020-065238

(51) Int. Cl.
*G01N 21/64*     (2006.01)
*G01N 33/00*     (2006.01)
(52) U.S. Cl.
CPC ......... *G01N 21/64* (2013.01); *G01N 33/0036* (2013.01)

(58) Field of Classification Search
CPC ................. G01N 21/64; G01N 33/0036
See application file for complete search history.

(56) References Cited

U.S. PATENT DOCUMENTS

| 11,176,510 B2 * | 11/2021 | Beasley ............... A23L 3/3418 |
| 2011/0221573 A1 | 9/2011 | Huat |
| | (Continued) | |

FOREIGN PATENT DOCUMENTS

| CN | 107202778 A | 9/2017 |
| CN | 108885737 A | 11/2018 |
| | (Continued) | |

OTHER PUBLICATIONS

Janssen et al., "Ethylene detection in fruit supply chains", Phil. Trans. R. Soc. A 372 (Year: 2014).*

(Continued)

*Primary Examiner* — Regis J Betsch
(74) *Attorney, Agent, or Firm* — Birch, Stewart, Kolasch & Birch, LLP

(57) ABSTRACT

A degradation status of a casing containing fresh items is to be grasped. An information processing device includes: an internal information acquisition unit acquiring internal information, which is information regarding an inside of a casing containing a fresh item in a refrigerated state or a frozen state; and a degradation information generation unit generating information regarding degradation of the casing based on the internal information acquired by the internal information acquisition unit. The internal information acquisition unit acquires, as the internal information, atmosphere information, which is information regarding an atmosphere inside the casing, and the degradation information generation unit generates the information regarding the degradation based on the atmosphere information.

13 Claims, 11 Drawing Sheets

(56) References Cited

U.S. PATENT DOCUMENTS

| | | | |
|---|---|---|---|
| 2013/0118195 A1* | 5/2013 | Ikemiya | F25B 49/005 |
| | | | 62/126 |
| 2018/0220665 A1* | 8/2018 | Savur | A23B 7/152 |
| 2019/0152674 A1 | 5/2019 | Boraso et al. | |

FOREIGN PATENT DOCUMENTS

| | | |
|---|---|---|
| JP | 61-50049 A | 3/1986 |
| JP | 2001-194318 A | 7/2001 |
| JP | 2009-18770 A | 1/2009 |
| JP | 2012-26675 A | 2/2012 |
| JP | 2017-89913 A | 5/2017 |
| WO | WO 2017/158579 A1 | 9/2017 |
| WO | WO 2017/172444 A1 | 10/2017 |
| WO | WO-2017172444 A1 * 10/2017 ......... G06Q 10/0832 |
| WO | WO 2018/074603 A1 | 4/2018 |

OTHER PUBLICATIONS

Opara et al., "Bruise damage measurement and analysis of fresh horticultural produce—A review", Postharvest Biology and Technology 91 (2014) 9-24 (Year: 2014).*

International Search Report for PCT/JP2021/014068 (PCT/ISA/210) dated Jun. 22, 2021.

Written Opinion of the International Searching Authority for PCT/JP2021/014068 (PCT/ISA/237) dated Jun. 22, 2021.

Extended European Search Report for European Application No. 21781748.5, dated Aug. 9, 2023.

* cited by examiner

INFORMATION PROCESSING DEVICE, STORAGE CONTAINER, AND NON-TRANSITORY COMPUTER READABLE MEDIUM

TECHNICAL FIELD

The present disclosure relates to an information processing device, a storage container, and a non-transitory computer readable medium.

BACKGROUND ART

Patent Document 1 discloses a configuration provided with a CCD camera photographing a surface to be inspected in synchronization with a pulse light source, and a damage detection device comparing illuminance of a dark part in an image of the photograph with a predetermined threshold, and, if the illuminance is lower than the threshold, issuing a damage detection signal.

CITATION LIST

Patent Literature

Patent Document 1: Japanese Patent Laid-Open No. 2001-194318

SUMMARY OF INVENTION

Technical Problem

Storage containers, such as containers containing fresh items, are provided with a casing and the fresh item is contained inside the casing in some cases.

Here, due to passage of time, the casing degrades to have holes or gaps. In this case, it becomes difficult to maintain the environment inside the casing at the environment that has been originally intended, and the freshness of the fresh items decreases.

An object of the present disclosure is to make it possible to grasp a degradation state of a casing containing fresh items.

Solution to Problem

An information processing device of the present disclosure includes: an internal information acquisition unit acquiring internal information, which is information regarding an inside of a casing containing a fresh item in a refrigerated state or a frozen state; and a degradation information generation unit generating information regarding degradation of the casing based on the internal information acquired by the internal information acquisition unit.

According to the information processing device, the status of degradation of the casing containing the fresh items can be grasped.

Here, the internal information acquisition unit may acquire, as the internal information, atmosphere information, which is information regarding an atmosphere inside the casing, and the degradation information generation unit may generate the information regarding the degradation based on the atmosphere information. In this case, the information regarding the degradation of the casing can be generated by obtaining information regarding the atmosphere inside the casing.

In addition, the internal information acquisition unit may acquire fresh item state information, which is information regarding a state of the fresh item contained in the casing, as the internal information, and the degradation information generation unit may generate the information regarding the degradation based on the fresh item state information. In this case, the information regarding the degradation of the casing can be generated by obtaining the information regarding the state of the fresh item contained in the casing.

In addition, the internal information acquisition unit may acquire operation status information, which is information regarding an operation status of an air conditioner that conditions air inside the casing, as the internal information, and the degradation information generation unit may generate the information regarding the degradation based on the operation status information acquired by the internal information acquisition unit. In this case, the information regarding the degradation of the casing can be generated by obtaining the information regarding the operation status of the air conditioner that conditions air inside the casing.

In addition, the internal information acquisition unit may further acquire atmosphere information, which is information regarding an atmosphere inside the casing, and the degradation information generation unit may generate the information regarding the degradation based on the operation status information and the atmosphere information acquired by the internal information acquisition unit. In this case, the information regarding the degradation of the casing can be generated by obtaining the information regarding the operation status of the air conditioner that conditions air inside the casing and the information regarding the atmosphere inside the casing.

In addition, the internal information acquisition unit may acquire a photographed image obtained by photographing the inside of the casing as the internal information, and the degradation information generation unit may analyze the photographed image to generate the information regarding the degradation. In this case, the information regarding the degradation of the casing can be generated by photographing the inside of the casing to obtain the photographed image thereof.

In addition, the degradation information generation unit may generate the information regarding the degradation based on the internal information acquired by the internal information acquisition unit when the casing is in a specific situation. In this case, as compared to the case in which the information regarding the degradation is generated based on the internal information obtained when the casing is not in the specific situation, the accuracy of information, when the information indicating that the casing has degraded is outputted, can be increased.

In addition, the degradation information generation unit may generate the information regarding the degradation based on the internal information acquired by the internal information acquisition unit when another casing is placed on the casing. In this case, the information regarding the degradation of the casing can be generated based on the internal information obtained under the situation in which the casing is likely to be deformed.

In addition, the degradation information generation unit may generate the information regarding the degradation based on the internal information acquired by the internal information acquisition unit when the casing is being transported. In this case, the information regarding the degradation of the casing can be generated based on the internal information obtained under the situation in which the casing is likely to be deformed.

In addition, the degradation information generation unit may generate the information indicating that the casing has degraded when the internal information includes information indicating that a predetermined specific event has occurred more than a predetermined number of times. In this case, as compared to the case in which the information indicating that the casing has degraded is generated when information indicating that the predetermined specific event has occurred only once is included in the internal information, the accuracy of information, when the information indicating that the casing has degraded is outputted, can be increased.

In addition, the degradation information generation unit may generate the information regarding the degradation for each of multiple locations inside the casing. In this case, the situation of degradation of the casing can be grasped individually for each of the multiple locations inside the casing.

In addition, an output unit may be further included, the output unit outputting the information regarding the degradation generated by the degradation information generation unit to a predetermined output destination. In this case, the generated information regarding the degradation can be outputted to the predetermined output destination.

In addition, the internal information acquisition unit may acquire, as the internal information, information regarding a heat reflux rate of the casing, and the degradation information generation unit may generate the information regarding the degradation of the casing based on a change in the heat reflux rate. In this case, the information regarding the degradation of the casing can be generated based on the information regarding the heat reflux rate.

In addition, the internal information acquisition unit may acquire an operation status of an appliance processing gas inside the casing as the internal information, and the degradation information generation unit may generate the information regarding the degradation of the casing based on a change in the operation status. In this case, the information regarding the degradation of the casing can be generated based on the operation status of the appliance processing the gas inside the casing.

Moreover, in the case where the present disclosure is viewed as a storage container, the storage container of the present disclosure includes: a casing containing a fresh item in a refrigerated state or a frozen state; and an information processing device processing information regarding the casing, wherein the information processing device is the information processing device described in any of the above descriptions. According to the storage container, the status of the degradation of the casing containing the fresh item can be grasped.

Moreover, in the case where the present disclosure is viewed as a program, the program of the present disclosure causes a computer to implement: an internal information acquisition function acquiring internal information, which is information regarding an inside of a casing containing a fresh item in a refrigerated state or a frozen state; and a degradation information generation function generating information regarding degradation of the casing based on the internal information acquired by the internal information acquisition function. According to the program, the status of the degradation of the casing containing the fresh item can be grasped.

DESCRIPTION OF EMBODIMENTS

Hereinafter, embodiments will be described with reference to drawings.

Figure 1:
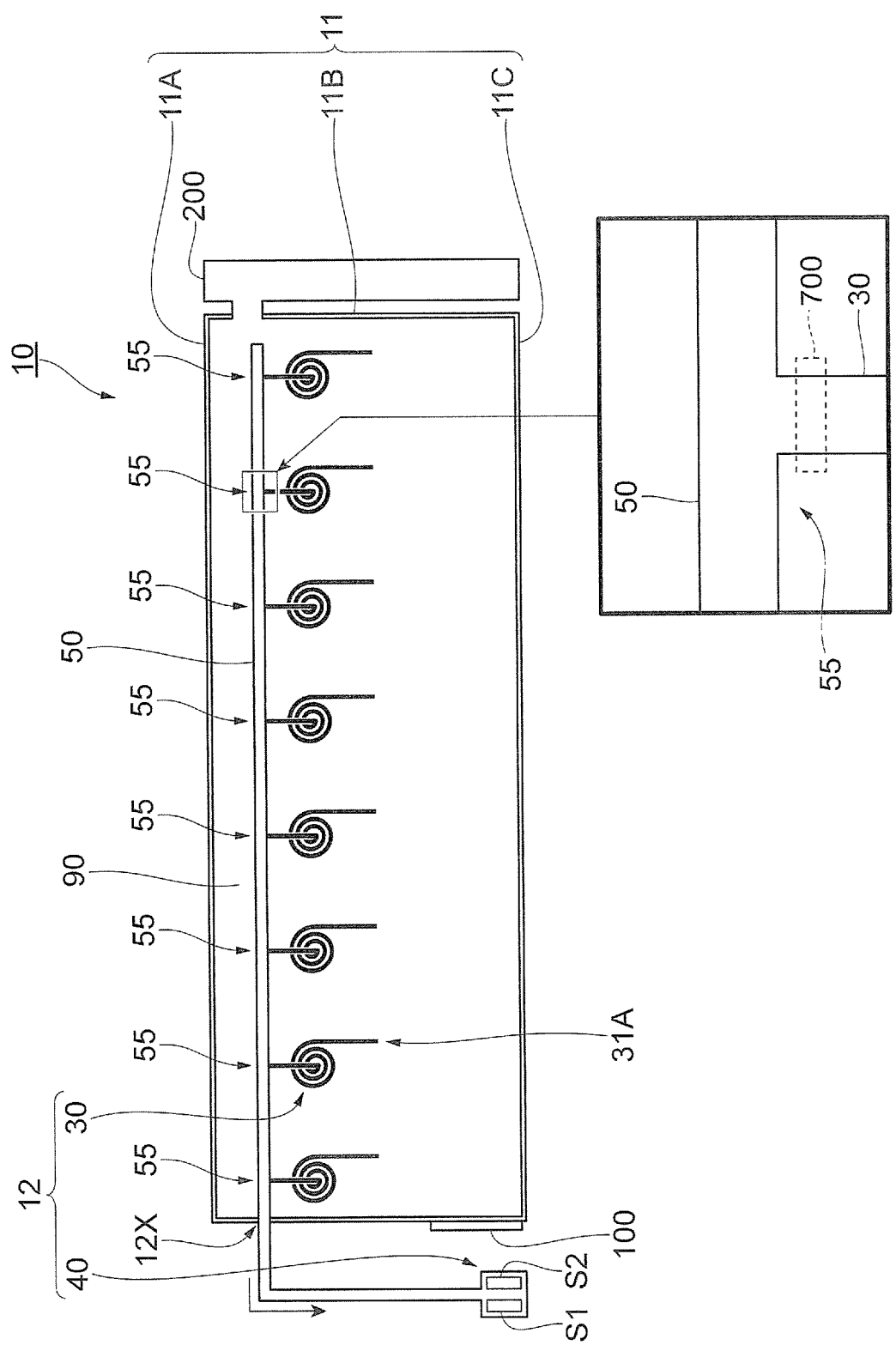
FIG. 1 is a diagram showing an example of a container.

FIG. 1 is a diagram showing an example of a container 10 related to the present embodiment.

The container 10, which is an example of a storage container, is used for transporting fresh items, and loaded on transportation equipment such as a ship, an aircraft, or a vehicle, to be transported to a destination.

Here, the "fresh item" refers to an item sold with importance placed on freshness under temperature control. Examples of the fresh items include green goods, fresh fish, and meat. Here, examples of the green goods include vegetables and fruits. The fresh items also include beverages such as milk and non-food products such as fresh flowers.

The present embodiment is provided with a detection unit 12 detecting the quality of gas in the container 10.

The detection unit 12 includes, as a main constituent, multiple collection members 30 collecting the gas, and a detection section 40.

The present embodiment is further provided with an information processing device 100 processing the detection results obtained by the detection section 40, or controlling valves 700, which will be described later, and so on.

The present embodiment is also provided with an air conditioner 200 setting the temperature inside the container 10 to a predetermined temperature.

In the present embodiment, the container 10 is supplied with cooled air by the air conditioner 200, and thereby the inside of the container 10 is brought into the refrigerated state or the frozen state. The container 10 of the present embodiment contains the fresh items in the refrigerated state or the frozen state.

The multiple collection members 30 are used for collecting the gas inside the container 10.

The collection member 30 is installed at each of multiple locations different from one another. More specifically, the multiple collection members 30 are disposed so that the positions thereof in the longitudinal direction of the container 10 are different from one another.

Note that the multiple collection members 30 may be disposed in the state where the positions thereof in the short direction of the container 10 are shifted from one another. In addition, the multiple collection members 30 may be disposed in the state where the positions thereof in the height direction are shifted from one another.

In the present embodiment, the collection members 30 are installed at the multiple locations, and each collection member 30 collects gas at each of the multiple locations.

The container 10 is provided with a rectangular parallelepiped casing 11 that divides the inside and the outside of the container 10. The multiple collection members 30 are supported by the casing 11.

Here, the "casing 11" refers to the portion that constitutes the main part of the container 10 and has a function to form the space to contain the objects.

In the present embodiment, the casing 11 contains the fresh items inside thereof.

The shape of the casing 11 is not limited to a rectangular parallelepiped or a cube, but may be a dome shape or a spherical shape, for example. In addition, the casing 11 is not limited to be configured by a single component, but may be configured by combining multiple components.

The casing 11 of the present embodiment is configured with a ceiling section 11A, side-wall sections 11B, and a bottom section 11C.

In the present embodiment, the fresh items (not shown) are contained in the rectangular parallelepiped space 90 enclosed by the ceiling section 11A, the side-wall sections 11B, and the bottom section 11C.

Moreover, in the present embodiment, the fresh items are contained in the space 90 in the refrigerated state or the frozen state as described above.

Each collection member 30 is composed of a resin material. In addition, each collection member 30 is configured with a flexible tubular member. This makes it possible in the present embodiment to adjust the positions of the collection members 30.

More specifically, each of the collection members 30 has an inlet 31A for sucking gas at the tip end portion thereof, and, in the present embodiment, the collection member 30 is deformed to make it possible to adjust the position of the inlet 31A.

To put it another way, the collection member 30 is supported by the casing 11, and has a free end on the end portion opposite to the side supported by the casing 11. In the present embodiment, the position of the end portion at the free end side can be adjusted.

Further, each of the collection members 30 is provided in a wound-up form, and by unwinding the collection member 30 or by winding the collection member 30, the length of the collection member 30 can be changed.

In addition, the collection member 30 is hanging down, and by unwinding the collection member 30 or by winding the collection member 30, the position of collecting the gas moves in the vertical direction.

As described above, the detection unit 12 is provided with a detection section 40 that detects the quality of the gas collected by the collection member 30.

In the present embodiment, the detection section 40 is not provided to correspond to each of the multiple collection members 30; accordingly, the number of installed detection sections 40 is less than the number of multiple collection members 30 that are installed. In other words, in the present embodiment, the multiple collection members 30 are installed more than the detection sections 40. In other words, in the present embodiment, the detection section 40 is being shared.

The detection section 40 as an example of a detecting unit includes a freshness sensor S1 and an environmental sensor S2.

The signals from the freshness sensor S1 and the environmental sensor S2 are outputted to the information processing device 100. In other words, the signal from the detection section 40 is transmitted to the information processing device 100.

The freshness sensor S1 acquires information regarding freshness of fresh items.

Here, an example of the freshness sensor S1 is a gas sensor that detects predetermined specific gases, such as ethylene gas and carbon dioxide.

In the case where the fresh items are vegetables or fruits, or in response to degradation of the fresh items, ethylene gas and carbon dioxide increase around the fresh items. By detecting the ethylene gas and carbon dioxide, decrease in freshness of the fresh items can be grasped.

In addition, examples of the freshness sensor S1 include a sensor that grasps fluorescence properties of the fresh items. More specifically, examples of the freshness sensor S1 include a sensor that grasps chlorophyll fluorescence of the fresh items.

Fresh items such as green goods sometimes contain materials that emit fluorescence when being irradiated with light having a short wavelength, such as ultraviolet light, and accordingly, by measuring the fluorescence, the freshness of the fresh items can be grasped.

In the case where the sensor that grasps the fluorescence properties of the fresh items is provided as the freshness sensor S1, the freshness sensor S1 is installed, for example, at a position facing the fresh items.

In addition, other than this, the respiration rate of the fresh items may be measured by use of the freshness sensor S1. More specifically, as the freshness sensor S1, at least one of a sensor detecting oxygen and a sensor detecting carbon dioxide may be installed to measure the respiration rate of the fresh items.

Here, respiration of fresh items, such as vegetables and fruits, is a chain of enzyme chemistries, serves as an index indicating that the higher the respiration rate (the amount of carbon dioxide generation or the amount of oxygen consumption per unit time), the progressively lower the freshness of the fresh items.

Here, the higher the temperature of the environment around the fresh items, the higher the respiration rate, and the higher the temperature of the environment around the fresh items, the higher the quality decline rate of the fresh items. By measuring the respiration rate of the fresh items, degradation in freshness of the fresh items can be grasped.

In addition, other than this, a near-infrared sensor may be used as the freshness sensor S1.

By degradation in freshness (maturing) of the fresh items, chlorophylls contained in the fresh items are decomposed, and the light absorption characteristics are changed. Based on the range of the change, degradation in freshness of the fresh items can be estimated. Note that, in the case where the near-infrared sensor is used as the freshness sensor S1, the near-infrared sensor is installed, for example, at a position facing the fresh items.

In addition, other than this, a sensor measuring electrical resistance of fresh items may be used as the freshness sensor S1. In the fresh items, cellular destruction is caused as the freshness is decreased, and the electrical resistance of the fresh items is reduced with the cellular destruction. Acquisition of the range of reduction in the electrical resistance makes it possible to grasp degradation in the freshness of the fresh items. Note that, in the case where the sensor measuring the electrical resistance of fresh items is used as the freshness sensor S1, and the sensor is disposed in contact with the fresh items.

The environmental sensor S2 acquires information regarding the environment in the casing 11.

An example of the environmental sensor S2 is a temperature sensor or a humidity sensor. In addition, examples of the environmental sensor S2 include a component sensor that detects specific components contained in the gas. Another example of the environmental sensor S2 is a pressure sensor.

The detection section 40 is installed outside the container 10.

In the case where the detection section 40 is installed outside container 10, the gas collected by the collection members 30 is moved to the outside of the container 10 and supplied to the detection section 40 provided outside the container 10.

In other words, the gas collected by the collection members 30 is moved to the outside the casing 11 that contains fresh items, and supplied to the detection section 40 provided outside the casing 11.

Note that the detection section 40 may be provided inside the casing 11, as will be described later, not limited to the outside of the casing 11. In addition, in the case where the detection section 40 is the sensor that grasps the fluorescence characteristics as described above, the detection section 40 is disposed inside the casing 11 at the position facing the fresh items.

Further, in the present embodiment, as shown in FIG. 1, there is provided a common duct 50, into which the gas collected by each of the collection members 30 flows (hereinafter, referred to as the "common duct 50").

The gas collected by each of the collected members 30 flows into the common duct 50 and is supplied to the detection section 40 through the common duct 50.

Further, the present embodiment is provided with a compressor and a pump (not shown) for sending the gas collected by the collection members 30 to the detection section 40.

The casing 11 is provided with an opening 12X for sending the gas collected by the collection members 30 to the outside of the container 10. In other words, the casing 11 is provided with the opening 12X for connecting the inside and the outside of the container 10.

The common duct 50 passes through the opening 12X to be provided from the inside to the outside of the casing 11.

In the present embodiment, the gas collected by the collection members 30 passes through the opening 12X to be supplied to the detection section 40. In other words, in the present embodiment, the space 90 inside the casing 11 is connected to the detection section 40 via the collection members 30 and the common duct 50.

Further, in the present embodiment, multiple connection sections 55, where the collection members 30 are connected to the common duct 50, are provided.

In the present embodiment, the detection section 40 is provided on the downstream side of the connection section 55 on the most downstream position in the moving direction of the gas toward the detection section 40.

Moreover, in the present embodiment, each of the connection sections 55 between the collection member 30 and the common duct 50 is provided with a valve 700 that connects and disconnects the collection member 30 and the common duct 50.

The valve 700 is, for example, an electromagnetic valve. Each of the valves 700 is controlled by a control section 201 (to be described later), and in each of the connection sections 55, the valve 700 is opened and closed.

In the present embodiment, of the multiple valves 700 that have been provided, for example, only one valve 700 is opened by the control section 201 (to be described later). In addition, the control section 201 sequentially switches the valves 700 to be opened.

Consequently, in the present embodiment, the gas is supplied from the collection members 300, which are part of the multiple collection members 30, to the detection section 40 sequentially.

In this case, in the present embodiment, information regarding degradation of the casing 11 can be generated for each of the multiple locations inside the casing 11 (details will be described later).

Figure 2:
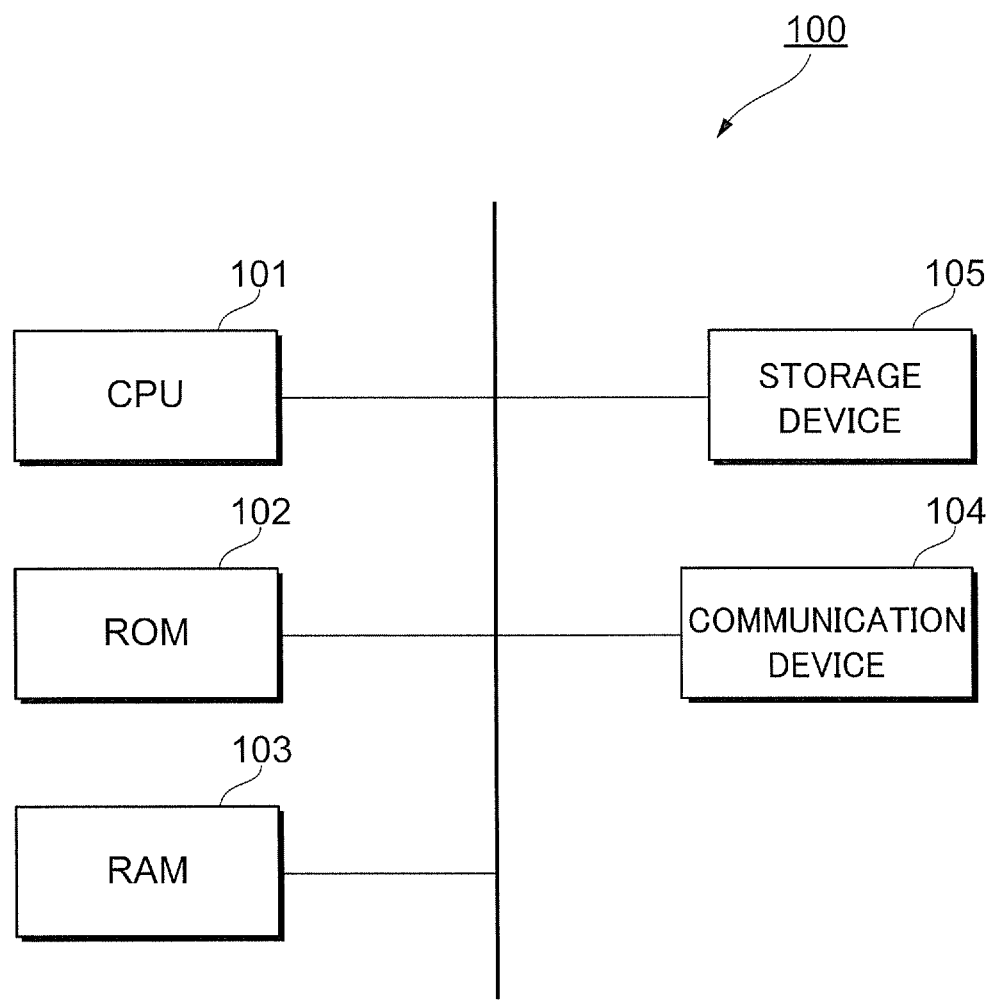
FIG. 2 is a diagram showing a hardware configuration of an information processing device.

FIG. 2 is a diagram showing a hardware configuration of the information processing device 100.

The information processing device 100 is provided with a CPU (Central Processing Unit) 101, as an example of a processor, a ROM (Read Only Memory) 102, and a RAM (Random Access Memory) 103. The information processing device 100 is also provided with a storage device 105, which is configured with a hard disk device and other devices, that stores information. Further, the information processing device 100 includes a communication device 104 (communication I/F) that communicates with the outside.

In addition, the information processing device 100 is provided with input devices used for inputting information, such as a keyboard, a mouse, etc., and a display device, such as a liquid crystal display or others.

The ROM 102 and the storage device 105 store programs to be executed by the CPU 101. The CPU 101 reads the programs stored in the ROM 102 and the storage device 105, and executes the programs using the RAM 103 as the work area.

The CPU 101 executes the programs stored in the ROM 102 and the storage device 105, to thereby achieve each functional section to be described later.

Here, the programs to be executed by the CPU 101 can be provided to the information processing device 100 in the state of being stored in a computer-readable recording medium, such as a magnetic recording medium (a magnetic tape, a magnetic disk, etc.), an optical recording medium (an optical disk, etc.), magneto optical recording medium or a semiconductor memory. In addition, the programs to be executed by the CPU 101 may be provided to the information processing device 100 using communication methods such as the Internet.

Figure 3:
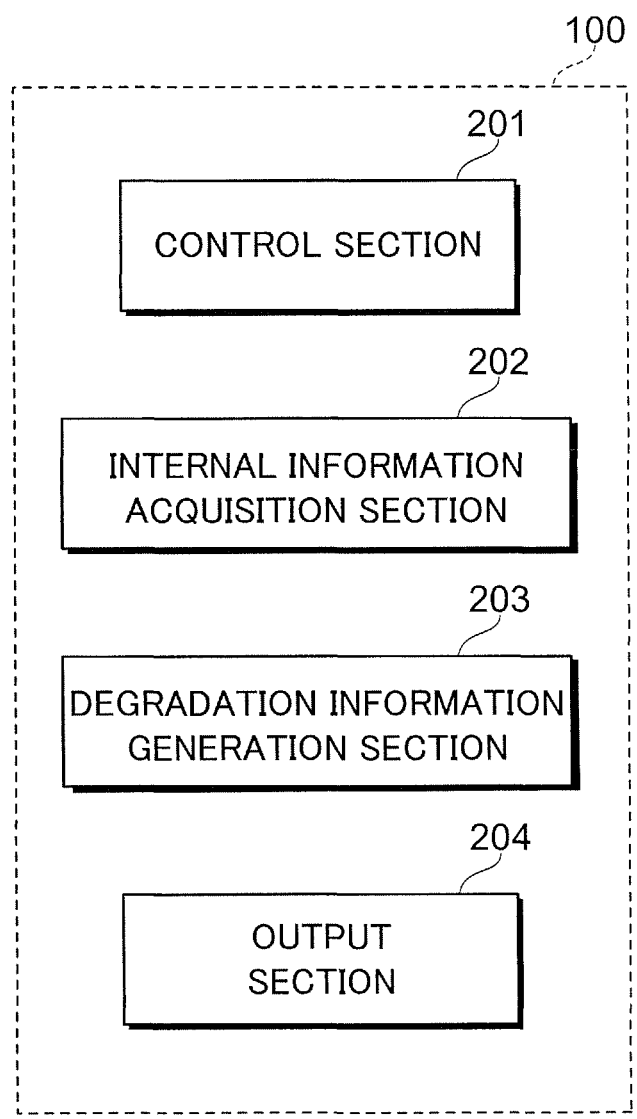
FIG. 3 is a block diagram showing functions of the information processing device.

FIG. 3 is a block diagram showing functions of the information processing device 100. Note that FIG. 3 shows a functional section related to generation of the information regarding the degradation of the casing 11.

The information processing device 100 of the present embodiment includes the control section 201, an internal information acquisition section 202, a degradation information generation section 203, and an output section 204. These functional sections are implemented by the CPU 101 executing the programs stored in the ROM 102 (refer to FIG. 2) and the storage device 105.

The control section 201 controls each part of the container 10, such as opening and closing the valves 700 as described above.

The internal information acquisition section 202, as an example of an internal information acquisition unit, acquires internal information regarding the inside of the casing 11.

Here, the "internal information" refers to information that can be acquired regarding the inside of the casing 11. Note that the internal information includes not only the very information obtained from the inside of the casing 11, but also information regarding devices that can affect the inside of the casing 11, such as information regarding the air conditioner 200.

The degradation information generation section 203, as an example of a degradation information generation unit, generates information regarding degradation of the casing 11.

The output section 204, as an example of an output unit, outputs the information regarding the degradation of the casing 11 generated by the degradation information generation section 203.

As described above, the internal information acquisition section 202 acquires the internal information, which is the information regarding the inside of the casing 11.

Then, in the present embodiment, the degradation information generation section 203 generates the information regarding the degradation of the casing 11 based on the internal information acquired by the internal information acquisition section 202.

More specifically, the internal information acquisition section 202 acquires, for example, atmosphere information that is information regarding an atmosphere inside the casing 11 as the internal information.

The degradation information generation section 203 generates the information regarding the degradation of the casing 11 based on the atmosphere information.

Specifically, the internal information acquisition section 202 acquires, for example, information outputted from the environmental sensor S2 as the atmosphere information.

Specifically, the internal information acquisition section 202 acquires the information outputted from the temperature sensor, the humidity sensor, the component sensor, the pressure sensor, and other sensors, as the atmosphere information.

The degradation information generation section 203 generates the information regarding the degradation of the casing 11 based on the information outputted from the temperature sensor, the humidity sensor, the component sensor, the pressure sensor, and other sensors.

Specifically, the degradation information generation section 203 generates the information indicating that the casing 11 has degraded, for example, in the case where the temperature inside the casing 11 is higher than a predetermined threshold.

More specifically, the degradation information generation section 203 generates the information indicating that the casing 11 has degraded in the case where the temperature acquired by the temperature sensor is higher than a predetermined threshold.

In addition, the degradation information generation section 203 generates the information indicating that the casing 11 has degraded, for example, in the case where the humidity inside the casing 11 is higher or lower than a predetermined threshold.

More specifically, the degradation information generation section 203 generates the information indicating that the casing 11 has degraded in the case where the humidity acquired by the humidity sensor is higher or lower than a predetermined threshold.

In the present embodiment, air is conditioned by the air conditioner 200 to keep the temperature inside the casing 11 lower than a predetermined temperature. In addition, in the present embodiment, air is conditioned by the air conditioner 200 to keep the humidity inside the casing 11 within a predetermined range.

On the other hand, if the casing 11 has degraded, for example, and, if the casing 11 has holes or gaps, the inside of the casing 11 is affected by the outside air.

In this case, the temperature inside the casing 11 is sometimes higher than the temperature that is originally expected, or the humidity inside the casing 11 is sometimes higher or lower than the humidity that is originally expected.

In the present embodiment, if such a situation exists, the degradation information generation section 203 generates the information indicating that the casing 11 has degraded.

Note that, in the present embodiment, a description will be given of a case in which information regarding the degradation of the casing 11 provided to the container 10 is generated.

By the way, the casing 11 to be the target of generation of information regarding the degradation is not limited to the casing 11 provided to the container 10. The casing 11 to be the target of generation of information regarding the degradation may be the casing 11 placed at a location other than the container 10.

Specifically, the casing 11 to be the target of generation of information regarding the degradation may be, for example, the casing 11 constituting a warehouse or the like.

Here, the casing 11 constituting the container 10 sometimes degrades with passage of time. Specifically, for example, the casing 11 may have holes or gaps in some cases.

In addition, a heat insulating material provided to the casing 11 degrades or a flow path provided to the casing 11 is blocked. Repetition of opening and closing the door in the container 10 may form gaps in the casing 11.

In this case, even if the air conditioner 200 is normally operating, there is a possibility that the inside of the casing 11 does not reach the appropriate temperature. In addition, there may be a situation in which the humidity does not reach the originally expected humidity.

In this case, in the present embodiment, the information regarding the degradation of the casing 11 is generated, and the administrator and the like can grasp that the casing 11 degrades by acquiring the information.

In addition, other than the above, for example, in the case where the component value detected by the component sensor is larger or smaller than a predetermined threshold, the degradation information generation section 203 may generate the information indicating that the casing 11 has degraded.

Here, if the casing 11 has holes or gaps, the amount of a specific gas decreases or increases inside the casing 11. In such a case, the degradation information generation section 203 generates the information indicating that the casing 11 has degraded.

More specifically, for example, to maintain the freshness of fresh items, carbon dioxide and oxygen are supplied to the inside of the casing 11 to adjust the concentration of carbon dioxide and the concentration of oxygen to a specific ratio in some cases.

In this case, if the casing 11 has holes or gaps, the ratio is changed, and the concentration of carbon dioxide and oxygen is changed.

In this case, in the present embodiment, the component sensor detects that the concentration of carbon dioxide and oxygen is changed. In this case, the degradation information generation section 203 generates the information indicating that the casing 11 has degraded.

In addition, other than the above, the internal information acquisition section 202 may acquire, for example, fresh item state information as the internal information. Here, the "fresh item state information" refers to information regarding the state of the fresh items contained in the casing 11.

In this case, the degradation information generation section 203 generates the information regarding the degradation of the casing 11 based on the fresh item state information.

More specifically, the internal information acquisition section 202 acquires, for example, information outputted from the freshness sensor S1 as the fresh item state information.

Then, the degradation information generation section 203 generates the information regarding the degradation based on the information outputted from the freshness sensor S1.

More specifically, the degradation information generation section 203 generates the information indicating that the casing 11 has degraded in the case where, for example, the information outputted from the freshness sensor S1 is information indicating that the fresh items have already degraded.

More specifically, the degradation information generation section 203 generates the information indicating that the casing 11 has degraded in the case where, for example, the concentration of ethylene gas or carbon dioxide outputted from the freshness sensor S1 exceeds a predetermined threshold.

More specifically, when the process is to be performed, a relationship table describing the relationship between the number of days elapsed since the placement of the fresh items in the casing 11 and the threshold for gas concentration is generated in advance, and the generated table is stored in the storage device 105 (refer to FIG. 2).

When the information regarding the concentration of ethylene gas or carbon dioxide (hereinafter, referred to as "gas concentration") is acquired from the freshness sensor S1, the degradation information generation section 203 calculates the number of days elapsed since the day on which the fresh items were actually placed in the casing 11 to the day on which the information regarding the gas concentration was acquired, and grasps thereof.

More specifically, in this case, the administrator or the like is asked to input information about the date of actually placing the fresh items in the casing 11, and the degradation information generation section 203 calculates and grasps the number of days elapsed since the date of placement to the date of acquiring the information regarding the gas concentration.

Then, the degradation information generation section 203 refers to the generated table to read and acquire a threshold corresponding to the grasped number of days elapsed.

The degradation information generation section 203 then determines whether or not the above-described acquired gas concentration is larger than the acquired threshold, and, in the case where the gas concentration is larger than the threshold, generates the information indicating that the casing 11 has degraded.

In the case where the casing 11 has holes or gaps, the temperature inside the casing 11 increases, and thereby the fresh items are more likely to degrade. In this case, more ethylene gas and carbon dioxide released from the fresh items can lead to increase in the concentration of ethylene gas and carbon dioxide, even though the number of days elapsed since the placement of the fresh items has been small yet.

In the present embodiment, if the concentration of ethylene gas and carbon dioxide are increased in spite of the still small number of days elapsed as described above, the degradation information generation section 203 generates the information indicating that the casing 11 has degraded.

In addition, the degradation information generation section 203 generates the information indicating that the casing 11 has degraded in the case where, for example, fluorescence properties of the fresh items outputted from the freshness sensor S1 meet a predetermined requirement.

More specifically, in the present embodiment, the degree of freshness of the fresh items can be grasped by measuring the fluorescence properties, such as chlorophyll fluorescence, as described above. In the case where the fluorescence properties of the fresh items outputted from the freshness sensor S1 meet the predetermined requirement, the information indicating that the casing 11 has degraded is generated.

More specifically, when the process is to be performed, similar to the above, a relationship table describing the relationship between the number of days elapsed since the placement of the fresh items in the casing 11 and the concrete threshold for the fluorescence properties is generated in advance, for example, and the generated table is stored in the storage device 105.

When the information regarding the fluorescence properties is acquired from the freshness sensor S1, similar to the above, the degradation information generation section 203 calculates the number of days elapsed since the day on which the fresh items were actually placed in the casing 11 to the day on which the information regarding the fluorescence properties was acquired, and grasps thereof.

Then, the degradation information generation section 203 refers to the relationship table to read and acquire a threshold corresponding to the grasped number of days elapsed.

The degradation information generation section 203 then generates the information indicating that the casing 11 has degraded in the case where a numeric value identified by the acquired information regarding the fluorescence properties is larger or smaller than the acquired threshold.

In addition, other than the above, the internal information acquisition section 202 may acquire the operation status information, which is information regarding the operation status of the air conditioner 200, from the air conditioner 200 to regard the operation status information as the internal information.

Then, in the case, the degradation information generation section 203 generates the information regarding the degradation based on the operation status information acquired by the internal information acquisition section 202.

More specifically, the internal information acquisition section 202 acquires, for example, power consumption of the air conditioner 200 as the internal information. In other words, the internal information acquisition section 202 acquires, for example, the power consumption of the air conditioner 200 as the operation status information.

Then, the degradation information generation section 203 generates the information regarding the degradation based on the power consumption acquired by the internal information acquisition section 202.

More specifically, in this case, the degradation information generation section 203 generates the information indicating that the casing 11 has degraded, in the case where, for example, the power consumption is larger than the predetermined threshold.

When the power consumption is large, it is expected that the temperature inside the casing 11 does not decrease due to holes or gaps in the casing 11, and thereby the air conditioner 200 operates more than necessary.

In this case, in the present embodiment, the degradation information generation section 203 generates the information indicating that the casing 11 has degraded.

Note that, in addition to the above, for example, information regarding the temperature of cooling air supplied to the inside of the casing 11 from the air conditioner 200 may be acquired as the operation status information. More specifically, in this case, for example, information regarding the set temperature of the cooling air is acquired from the air conditioner 200.

The degradation information generation section 203 then generates the information indicating that the casing 11 has degraded in the case where, for example, the temperature identified by the information regarding the acquired set temperature is smaller than the predetermined threshold.

If the casing 11 has the holes or gaps, the temperature inside the casing 11 increases; with this, the air conditioner 200 sometimes changes the set temperature to set the lower set temperature. In this case, the degradation information generation section 203 generates the information indicating that the casing 11 has degraded.

In addition, as the operation status information, other than the above, the number of revolutions of fans provided to the air conditioner 200, the operation status of a compressor, and the like may be grasped.

In this case, the degradation information generation section 203 generates the information indicating that the casing 11 has degraded in the case where the number of revolutions of fans exceeds the predetermined threshold, or the compressor is excessively operating.

In addition, as the operation status information, other than the above, an operation status of a supply device (not shown) that supplies carbon dioxide or oxygen to the casing 11, not limited to the air conditioner 200, may be grasped.

Then, In this case, the degradation information generation section 203 generates the information indicating that the casing 11 has degraded in the case where the grasped operation status meets a specific requirement.

More specifically, similar to the above, the degradation information generation section 203 generates the information indicating that the casing 11 has degraded in the case where, for example, the power consumption of the supply device exceeds the predetermined threshold.

In the present embodiment, in some cases, the supply device is used to supply carbon dioxide and oxygen to the inside of the casing 11, to thereby adjust the concentration of carbon dioxide and the concentration of oxygen inside the casing 11 to a specific ratio.

In this case, if there are holes or gaps in the casing 11, the concentration of carbon dioxide and oxygen cannot be a predetermined concentration, and the power consumption of the supply device increases.

In this case, in the present embodiment, similar to the above, the degradation information generation section 203 generates the information indicating that the casing 11 has degraded.

In addition, other than the above, the internal information acquisition section 202 may acquire both the above-described operation status information and atmosphere information as the internal information.

In this case, the degradation information generation section 203 generates the information regarding the degradation of the casing 11 based on both the operation status information and the atmosphere information.

More specifically, in this case, the degradation information generation section 203 generates the information indicating that the casing 11 has degraded, in the case where, for example, the temperature obtained by the temperature sensor is higher than the threshold despite that the air conditioner 200 is operating over the predetermined time.

In addition, the degradation information generation section 203 generates the information indicating that the casing 11 has degraded in the case where, for example, the temperature obtained by the temperature sensor is higher than the threshold despite that the power consumption of the air conditioner 200 is larger than the predetermined threshold.

In addition, other than the above, the degradation information generation section 203 may generate the information indicating that the casing 11 has degraded in the case where, for example, the information obtained by the freshness sensor S1 indicates that the fresh items have already degraded despite that the air conditioner 200 is normally operating.

Moreover, the internal information acquisition section 202 may acquire a photographed image obtained by photographing the inside of the casing 11 as the internal information. Note that, in this case, an imaging device (not shown) that photographs the inside of the casing 11 is installed inside the casing 11. Here, the imaging device is, for example, a CCD (Charge Coupled Device) and a CMOS (Complementary Metal Oxide Semiconductor).

In this case, the degradation information generation section 203 generates the information regarding the degradation of the casing 11 upon analyzing the photographed image acquired by the imaging device.

More specifically, in this case, the degradation information generation section 203 analyzes the photographed image to determine whether or not there are holes or gaps in the casing 11.

More specifically, when a hole or a gap occurs in the casing 11, the brightness of the area increases; consequently, the degradation information generation section 203 determines that the casing 11 has a hole or a gap in the case where, for example, the brightness of a part of the photographed image increases.

Then, in this case, the degradation information generation section 203 generates the information indicating that the casing 11 has degraded.

Note that, other than the above, for example, a result of irradiating an inner wall surface of the casing 11 with light from a light source and receiving the reflected light may be acquired as the internal information.

If there are holes or gaps in the casing 11, the reflected light cannot be obtained or the reflected light is weakened; accordingly, it is possible to grasp that the casing 11 has holes or gaps.

In addition, other than the above, the degradation information generation section 203 may generate the information regarding the degradation based on the internal information acquired by the internal information acquisition section 202 when the casing 11 is in a specific situation.

More specifically, as described above, the internal information acquisition section 202 acquires, as the internal information, the fresh item state information, the operation status information, the atmosphere information, the photographed image, and so on.

The degradation information generation section 203 may generate the information regarding the degradation based on such information acquired by the internal information acquisition section 202 when the casing 11 is in a specific situation.

More specifically, the degradation information generation section 203 generates the information regarding the degradation based on the internal information acquired by the internal information acquisition section 202 when, for example, another casing 11 is placed on the casing 11.

To put it another way, the degradation information generation section 203 may generate the information regarding the degradation based on the internal information acquired by the internal information acquisition section 202 when another container 10 is placed on the container 10.

In other words, the degradation information generation section 203 may generate the information regarding the degradation based on the internal information acquired by the internal information acquisition section 202 when the container 10 is actually used.

In this case, the degradation information generation section 203 generates the information regarding the degradation of the container 10 based on the internal information obtained under the situation in which the casing 11 is deformed and the holes and gaps occurring in the casing 11 are enlarged.

In the case where another casing 11 is placed on the casing 11, the target casing 11 positioned below is likely to be deformed due to the weight of the other casing 11. In this case, if the target casing 11 has holes or gaps, the holes or gaps are enlarged.

In this case, the situation in which there are holes or gaps in the casing 11 is reflected in the internal information acquired by the internal information acquisition section 202.

In this case, even though the holes and gaps occurring in the casing 11 are small, the information indicating the occurrence of degradation is likely to be generated in the degradation information generation section 203.

Note that whether or not another casing 11 is placed on the casing 11 can be determined by, for example, installing a load cell on each casing 11 and obtaining an output from the load cell.

In addition, whether or not another casing 11 is placed on the casing 11 may be determined based on information indicating that another casing 11 is placed on the casing 11 inputted by the administrator or the like, who has been asked to input the information.

In addition, other than the above, the degradation information generation section 203 may generate the information regarding the degradation of the casing 11 based on the internal information acquired by the internal information acquisition section 202 when the container 10 is being transported.

In this case, it is possible to obtain the internal information under the situation in which the container 10 is loaded on a cargo ship, an external force is applied to the casing 11, and the casing 11 is easily deformed.

In this case, similar to the above, the situation in which there are holes or gaps in the casing 11 is reflected in the internal information acquired by the internal information acquisition section 202.

Then, in this case, similar to the above, even though the holes and gaps occurring in the casing 11 are small, the information indicating the occurrence of degradation is likely to be generated in the degradation information generation section 203.

Note that whether or not the casing 11 is transported can be determined based on, for example, the degree of change in the position, which is identified by positional information obtained by GPS, per unit time.

More specifically, in this case, the GPS is installed in the container 10. Then, the degree of change in position, which is identified by the positional information obtained by the GPS, per unit time is grasped, and, in the case where the degree exceeds a predetermined threshold, it is determined that the container 10 is being transported.

In addition, other than the above, the degradation information generation section 203 may generate the information indicating that the casing 11 has degraded in the case where information indicating that a predetermined specific event has occurred more than a predetermined number of times is included in the internal information.

More specifically, the degradation information generation section 203 generates the information indicating that the casing 11 has degraded in the case where, for example, information indicating that the temperature inside the container 10 exceeds the threshold three times is included in the internal information.

More specifically, in this case, the degradation information generation section 203 analyzes the internal information obtained by the internal information acquisition section 202. Then, the degradation information generation section 203 generates the information indicating that the casing 11 has degraded in the case where, for example, information indicating that the temperature inside the container 10 exceeds the threshold three times is included in the internal information.

In this case, accuracy of the information indicating that the casing 11 has degraded is increased as compared to, for example, the case in which the information indicating that the casing 11 has degraded is generated based on information indicating that the temperature inside the container 10 exceeds the threshold once.

In addition, other than the above, the degradation information generation section 203 may generate the information regarding the degradation for each of the multiple locations inside the casing 11.

More specifically, in the configuration example of the present embodiment, as described above, the valve 700 is provided at each connection section 55 between the collection member 30 and the common duct 50, and the gas can be supplied to the detection section 40 individually at each installation location of the collection member 30.

In this case, the internal information acquisition section 202 can acquire the internal information at each of the multiple locations inside the casing 11.

In this case, the degradation information generation section 203 generates the information regarding the degradation based on each internal information acquired by the internal information acquisition section 202.

In this case, the degradation information generation section 203 generates information indicating whether or not the casing 11 has degraded for each location where the collection member 30 is installed.

To put it another way, in this case, the degradation information generation section 203 generates information indicating whether or not the casing 11 has degraded for each of the multiple locations inside the casing 11.

Note that, in the above, the description has been given of the case, in which the information indicating that the casing 11 has degraded is generated as the information regarding the degradation, as an example; however, the information to be generated is not limited thereto.

The degradation information generation section 203 may generate information indicating the degree of degradation in place of, or, in addition to the information indicating that the casing 11 has degraded.

More specifically, the degradation information generation section 203 may generate information indicating the degree of degradation in accordance with the degree of numerical values identified by the internal information acquired by the internal information acquisition section 202.

More specifically, the degradation information generation section 203, for example, may grasp the degree of degradation by a numerical value within the range of 0 to 100, and output the numerical value.

In the present embodiment, as described above, the degradation information generation section 203 generates the information regarding the degradation of the casing 11.

When the degradation information generation section 203 generates the information regarding the degradation, in the present embodiment, the output section 204 (refer to FIG. 3) outputs the information regarding the degradation to a predetermined destination.

Specifically, the output section 204 outputs the information regarding the degradation, for example, to a PC (personal computer) or a mobile terminal of the administrator of the container 10.

Moreover, for example, in the case where the container 10 is provided with a display device, the output section 204 outputs the information regarding the degradation to the display device.

This allows the administrator and the like of the container 10 to know the information regarding the degradation of the container 10.

In addition, other than the above, in the case where the output section 204 outputs the information indicating that the casing 11 has degraded, the output section 204 may further output the information indicating warning. In addition, other than the above, the output section 204 may output the information encouraging a checkup of the casing 11.

Here, in the present embodiment, the degradation itself of the casing 11 is not directly detected; consequently, it can also be expected that the casing 11 has not degraded in actuality. In other words, it is also be expected that the fresh items have degraded by a factor other than the degradation of the casing 11.

In this case, if the information encouraging the checkup of the casing 11 is outputted as described above, the possibility of finding factors that degrade the fresh items, which are other than the degradation of the casing 11, increases.

For example, the possibility of finding the other factors, such as a situation in which the container 10 is placed at a poorly ventilated position, or a situation in which the air conditioner 200 has troubles, increases.

(Others)

In the above, the description has been given of the case in which the detection section 40 is provided outside the container 10. To put it another way, in the above, the description has been given of the case in which the freshness sensor S1 and the environmental sensor S2 are provided outside the container 10.

Figure 4:
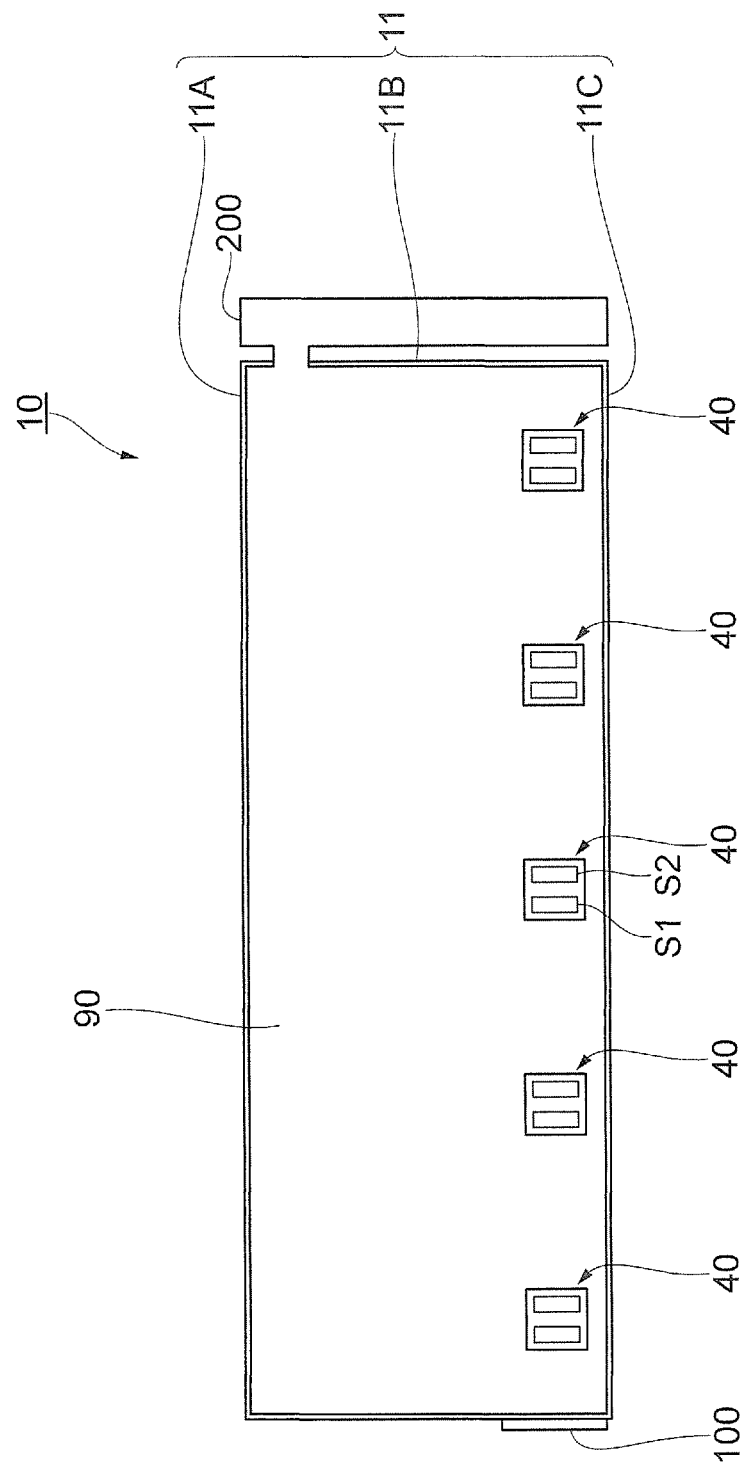
FIG. 4 is a diagram showing another configuration example of the container.

By the way, the position of placement of the detection section 40 is not limited thereto, and the detection section 40 may be provided inside the container 10, as shown in FIG. 4 (the diagram showing another configuration example of the container 10).

In the configuration example shown in FIG. 4, installation of the collection members 30 is canceled, and the detection sections 40 are placed at the respective locations where the collection members 30 were installed. In this case, in similar to the above, the information regarding the degradation of the casing 11 can be generated for each of the multiple locations.

Figure 5:
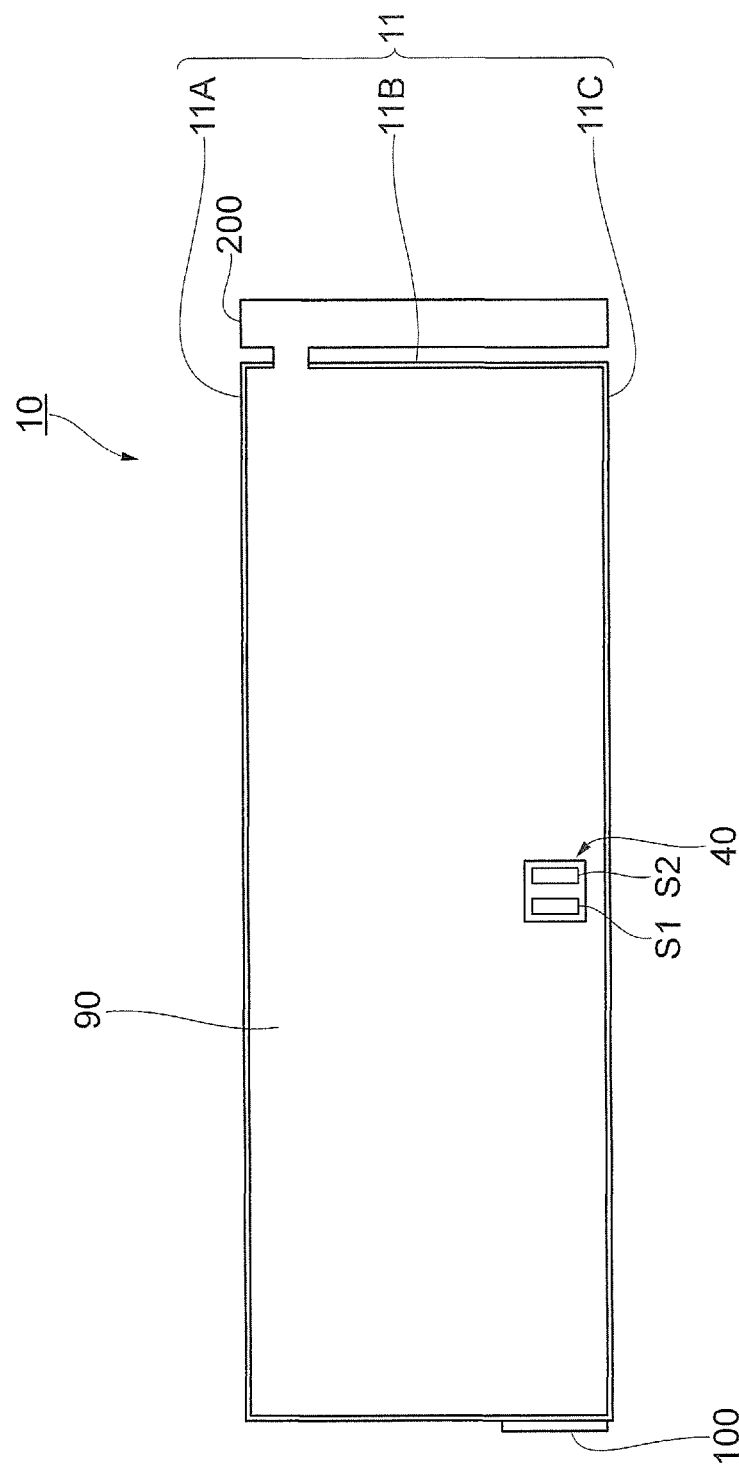
FIG. 5 is a diagram showing still another configuration example of the container.

In addition, in the case where the detection sections 40 are provided inside the container 10, only one detection section 40 may be provided inside the container 10 as shown in FIG. 5 (the diagram showing another configuration example of the container 10).

Note that, in the case where only one detection section 40 is provided as described above, it is preferable to provide the one detection section 40 at the center portion of the container 10 in the longitudinal direction.

In addition, in the above, acquisition of the internal information and generation of the information regarding the degradation of the casing 11 have been performed by the information processing device 100 provided to the container 10.

By the way, not limited thereto, the information processing device 100 may be installed separately from the container 10 to acquire the internal information and generate the information regarding the degradation of the casing 11.

Moreover, in the above, the description has been given of the case in which the pieces of information obtained by the detection sections 40 are sequentially supplied to the internal information acquisition section 202; however, not limited thereto, the information obtained by the detection sections 40 may be temporarily stored in a memory provided to the detection section 40.

Then, for example, at specific timing, such as the timing of taking the fresh items out of the container 10, the stored information may be provided from the memory to the information processing device 100.

In addition, the degradation information generation section 203 may generate the information regarding the degradation of the casing 11 based on the plural pieces of internal information obtained by the internal information acquisition section 202.

More specifically, the degradation information generation section 203 may generate the information regarding the degradation of the casing 11 based on the plural pieces of internal information sequentially acquired by the internal information acquisition section 202.

In other words, the degradation information generation section 203 may generate the information regarding the degradation of the casing 11 based on each of the plural pieces of internal information acquired sequentially and in chronological order by the internal information acquisition section 202.

More specifically, in this case, the degradation information generation section 203 sequentially acquires the pieces of internal information acquired by the internal information acquisition section 202. Then, in the case where the latest internal information that has been acquired is the information indicating that the casing 11 has degraded, the degradation information generation section 203 generates and outputs the information indicating that the casing 11 has degraded.

In this case, the inside of the casing 11 is always monitored substantially; therefore, if degradation occurs in the casing 11, it is possible to provide the information indicating that the casing 11 has degraded to the administrator or the like at earlier timing.

In addition, other than the above, outputs from the detection sections 40 provided to the respective containers 10, which are the outputs of the respective multiple containers 10, are acquired, and the multiple outputs that have been obtained may be compared.

Then, in the case where the contents of one output are different from those of each of the other outputs, the container 10 where the detection section 40, from which the one output has been obtained, is installed may be identified.

In this case, at the identified container 10, occurrence of abnormality, such as the degradation of the casing 11, can be detected.

Here, in the case where there are multiple containers 10 under the same conditions, when abnormality occurs in one container 10, the detection result by the detection section 40, which is obtained in the one container 10, is different from the detection result by the detection section 40, which is obtained in each of the other containers 10.

In this case, it is expected that abnormality, such as the degradation of the casing 11, occurs in the one container 10, and, in the process of the present embodiment, the occurrence of the abnormality can be grasped.

Next, specific examples of processes carried out in the present embodiment will be described.

Figure 6:
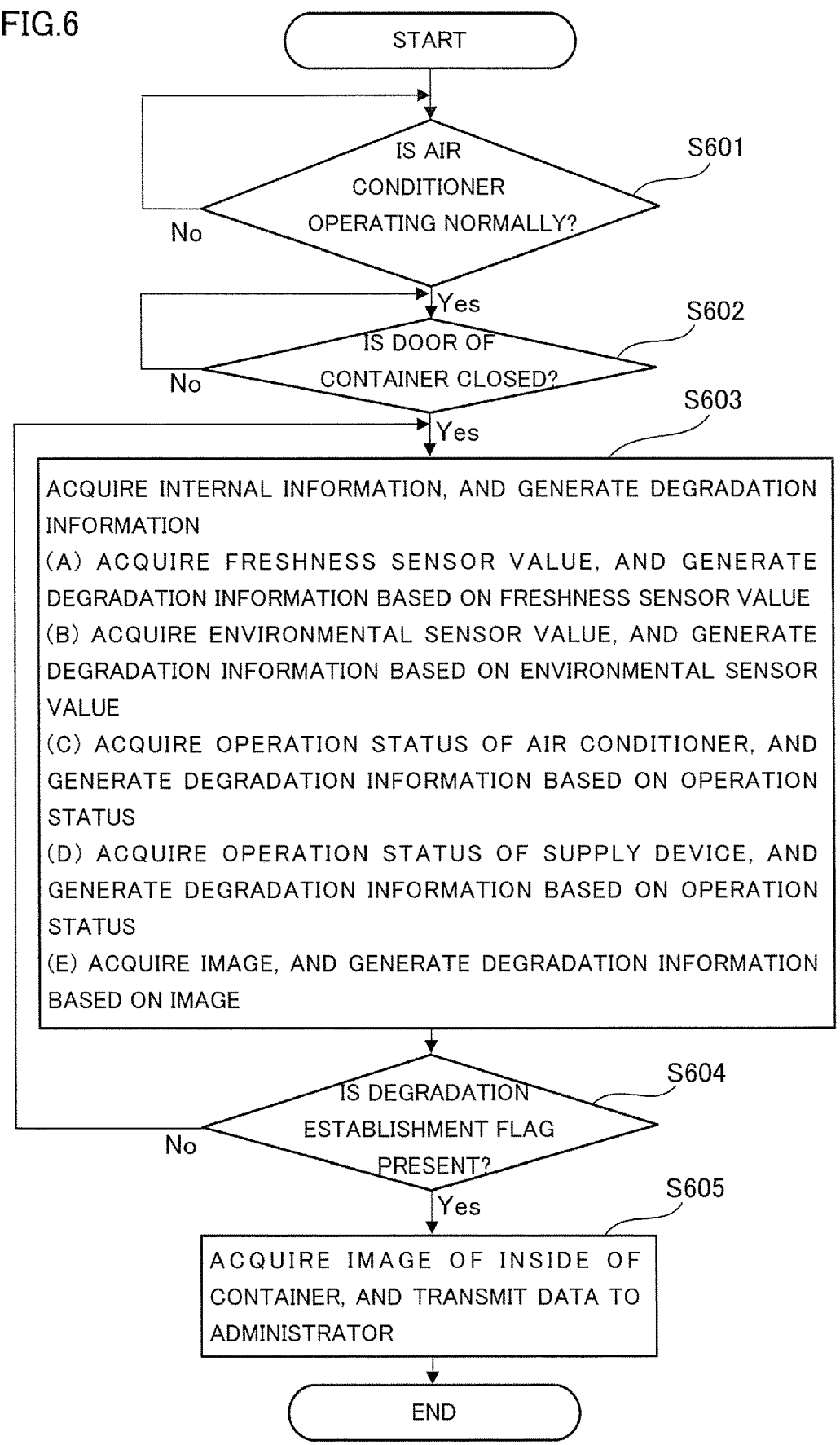
FIG. 6 is a flowchart showing an example of a process flow.

FIG. 6 is a flowchart showing an example of a process flow carried out in the present embodiment.

In the present embodiment, when a process is started, first, it is determined whether or not the air conditioner 200 is operating normally (step S601). In other words, whether or not the appliances, such as a freezing machine, are normally operating is determined.

Then, if the appliances are operating normally, it is determined whether or not the door of the container 10 is closed (step S602).

Then, in the case where it is determined in step S602 that the door of the container 10 is closed, an acquisition process of the internal information by the internal information acquisition section 202 and a generation process of the degradation information by the degradation information generation section 203 are performed (step S603).

More specifically, in the process of step S603, the internal information acquisition section 202 and the degradation information generation section 203 carry out the following processes (A) to (E).

(A) The internal information acquisition section 202 and the degradation information generation section 203 acquire the freshness sensor value, which is the value obtained by the freshness sensor S1, and generate the degradation information based on the freshness sensor value.

(B) The internal information acquisition section 202 and the degradation information generation section 203 acquire the environmental sensor value, which is the value obtained by the environmental sensor S2, and generate the degradation information based on the environmental sensor value.

(C) The internal information acquisition section 202 and the degradation information generation section 203 acquire the operation status of the air conditioner 200, and generate the degradation information based on the operation status.

(D) The internal information acquisition section 202 and the degradation information generation section 203 acquire the operation status of the supply device that supplies carbon dioxide and the like to the container 10, and generate the degradation information based on the operation status.

(E) The internal information acquisition section 202 and the degradation information generation section 203 acquire the image obtained by the imaging device, and generate the degradation information based on the image.

In the case where the degradation information generation section 203 determines that the degradation occurs in the container 10 in step S603, the degradation information generation section 203 sets a degradation establishment flag, which is a flag indicating that the container 10 is degrading, in step S603.

Then, in step S604, it is determined whether or not the degradation establishment flag is set, and in the case where the degradation establishment flag is set, the process proceeds to step S605.

In the process of step S605, the inside of the container 10 is photographed by using the imaging device installed inside the container 10 to acquire an image of the inside of the container 10.

In addition, in the process of step S605, a message to the effect that the degradation establishment flag is set (to the effect that the container 10 is degrading) and data indicating that the degradation occurs are transmitted to the administrator.

Here, examples of data indicating that the degradation occurs include the number of degradation establishment flags, information acquired by the internal information acquisition section 202, and the image obtained by the imaging device.

This allows the administrator to grasp the degradation of the container 10, and the degree of the degradation.

Note that, in the case where the container 10 is used as a maritime container, since the container 10 is continuously used over multiple voyages, the internal information acquisition section 202 acquires information of multiple voyages in this case.

In addition, in the present embodiment, the more the number of degradation establishment flags described above is notified to the administrator, the more the possibility of actual degradation of the container 10 increases, and the more the number of degradation establishment flags is, the more the accuracy of actual degradation of the container 10 increases.

Figure 7:
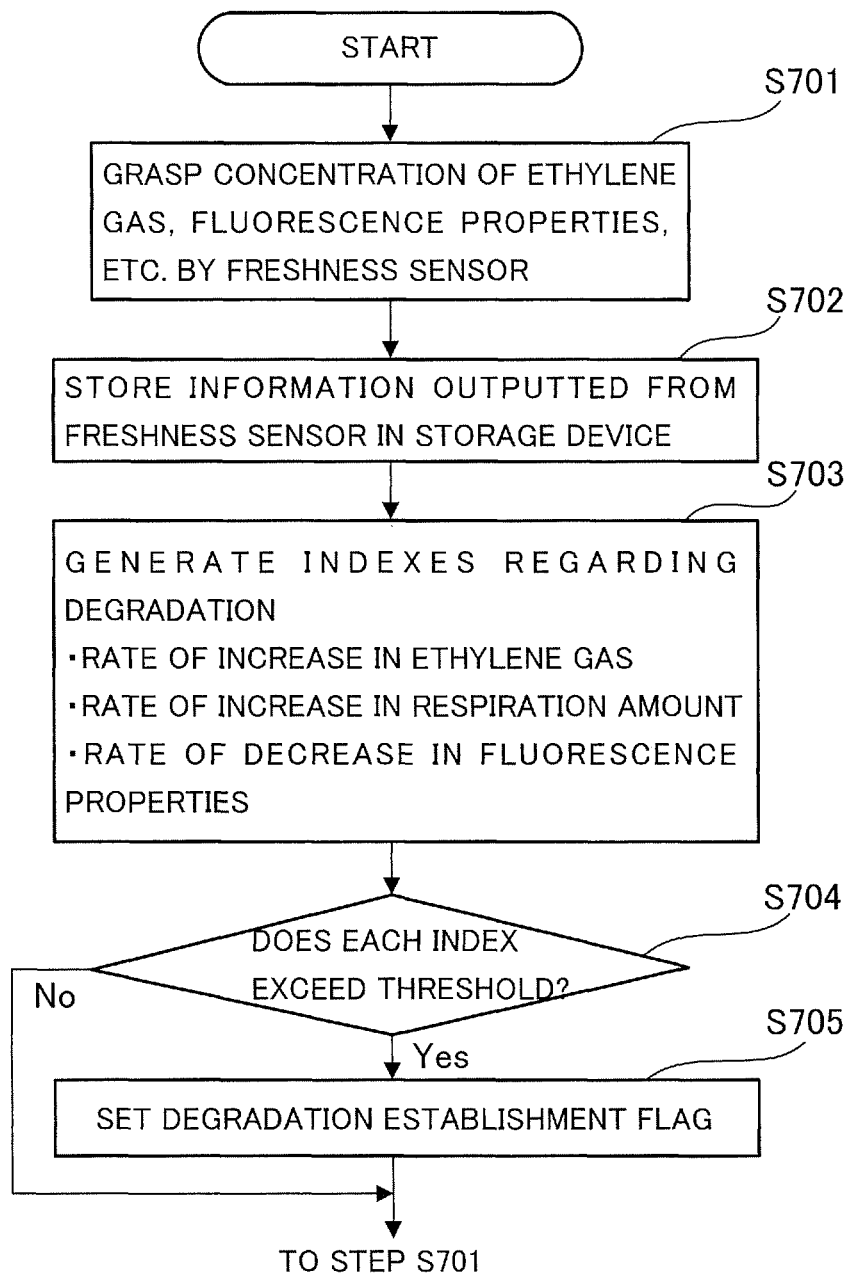
FIG. 7 is a flowchart showing a flow of processes performed in an acquisition process of a freshness sensor value and a generation process of degradation information based on the freshness sensor value.

FIG. 7 is a flowchart showing a flow of processes performed in the acquisition process of the freshness sensor value and the generation process of the degradation information based on the freshness sensor value in the above-described (A).

In the present embodiment, the concentration of ethylene gas, oxygen, carbon dioxide, and the like can be grasped by the freshness sensor S1 (step S701). In addition, in the present embodiment, the fluorescence properties can be grasped by the freshness sensor S1 (step S701).

Then, in the present embodiment, the internal information acquisition section 202 acquires these pieces of information sequentially outputted from the freshness sensor S1, and stores these pieces of information in the storage device 105 (refer to FIG. 2) (step S702).

Next, in the present embodiment, the internal information acquisition section 202 reads the information from the storage device 105 every elapse of a predetermined amount of time, and based on the information, generates an index of degradation of the container 10 (step S703).

Specifically, the internal information acquisition section 202 generates, for example, information regarding a rate of increase in ethylene gas as an index of degradation of the container 10.

Specifically, the internal information acquisition section 202 generates information regarding the rate of increase in ethylene gas based on the concentration of ethylene gas at specific timing and the concentration of ethylene gas at specific timing prior to the above specific timing.

More specifically, the internal information acquisition section 202 reads the information regarding the concentration of ethylene gas from the storage device 105.

Then, the internal information acquisition section 202 generates the information regarding the rate of increase in ethylene gas based on the concentration of ethylene gas at specific timing and the concentration of ethylene gas at specific timing prior to the above specific timing.

Then, the process proceeds to step S704, and the degradation information generation section 203 determines whether or not the rate of increase in ethylene gas exceeds a predetermined threshold.

In the case where the rate of increase in ethylene gas exceeds the predetermined threshold, the degradation information generation section 203 determines that the container 10 is degrading, and sets the degradation establishment flag, which is a flag indicating that the container 10 is degrading (step S705).

Note that, after the process in step S705, the processes in and after step S701 are performed again. In addition, in the case where it is determined in step S704 that the rate of increase in ethylene gas does not exceed the predetermined threshold, the processes in and after step S701 are also performed again.

Moreover, other than the above, in the process in step S703, for example, information regarding the rate of increase in the respiration amount may be generated as an index of degradation of the container 10.

Specifically, the internal information acquisition section 202 generates information regarding a rate of decrease in the concentration of oxygen and a rate of increase in the concentration of carbon dioxide as the information regarding the rate of increase in the respiration amount.

Specifically, the internal information acquisition section 202 generates information regarding the rate of decrease in the concentration of oxygen and the rate of increase in the concentration of carbon dioxide based on the concentration of oxygen and the concentration of carbon dioxide at specific timing and the concentration of oxygen and the concentration of carbon dioxide at specific timing prior to the above specific timing.

Then, the process proceeds to step S704, and the degradation information generation section 203 determines whether or not the rate of increase in the respiration amount (the rate of decrease in the concentration of oxygen and the rate of increase in the concentration of carbon dioxide) exceeds a predetermined threshold.

In the case where the rate of increase in the respiration amount exceeds the predetermined threshold, the degradation information generation section 203 determines that the container 10 is degrading, and sets the degradation establishment flag (step S705).

Moreover, other than the above, in the process in step S703, information regarding the rate of decrease in the fluorescence properties may be generated as an index of degradation of the container 10.

Specifically, the internal information acquisition section 202 generates information regarding the rate of decrease in the fluorescence properties based on the value of the amount of chlorophyll fluorescence at specific timing and the value of the amount of chlorophyll fluorescence at specific timing prior to the above specific timing.

Then, the process proceeds to step S704, and the degradation information generation section 203 determines whether or not the rate of decrease in the fluorescence properties exceeds a predetermined threshold.

In the case where the rate of decrease in the fluorescence properties exceeds the predetermined threshold, the degradation information generation section 203 determines that the container 10 is degrading, and sets the degradation establishment flag (step S705).

Figure 8:
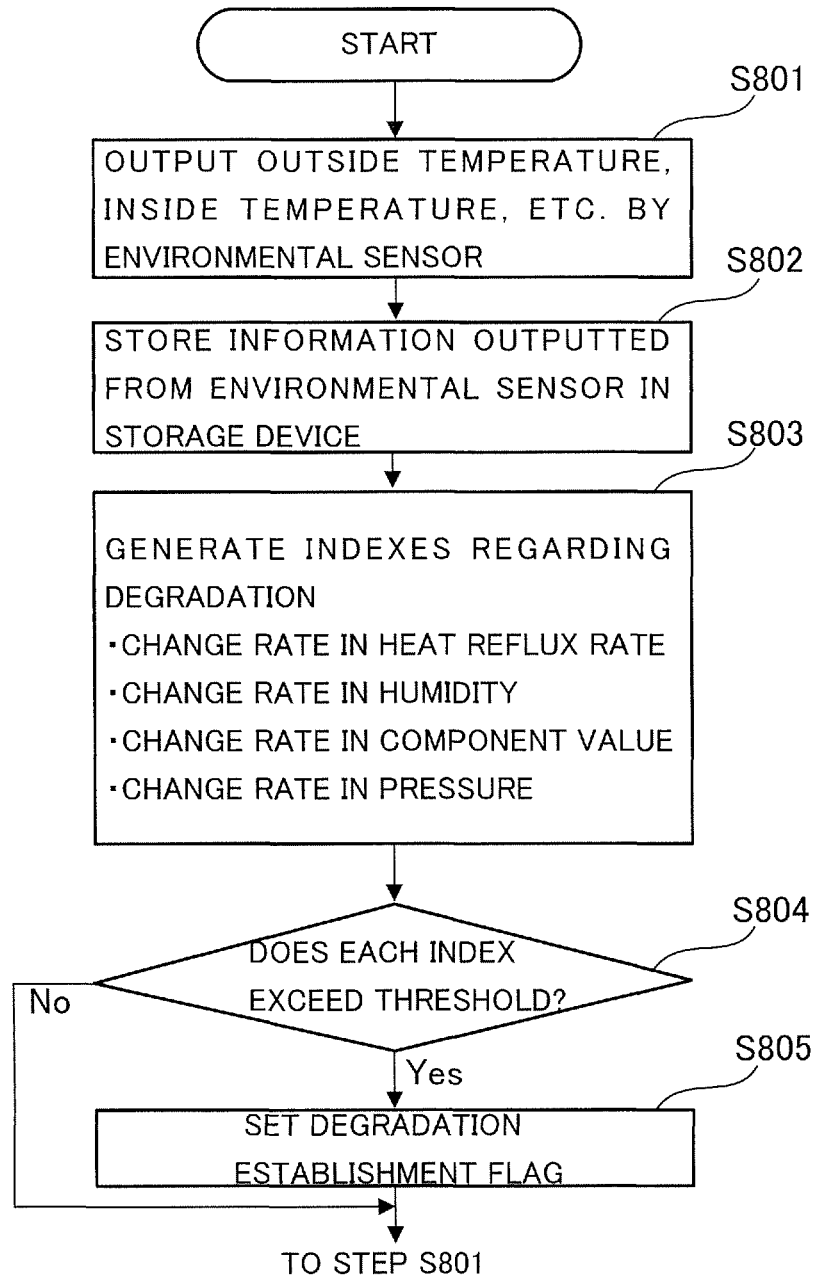
FIG. 8 is a flowchart showing a flow of an acquisition process of an environmental sensor value and a generation process of degradation information based on the environmental sensor value.

FIG. 8 is a flowchart showing a flow of the acquisition process of the environmental sensor value and generation process of degradation information based on the environmental sensor value in the above-described (B).

In the process of (B), the environmental sensor S2 sequentially outputs pieces of information regarding the outside temperature, the inside temperature, the humidity, the gas component value, and the air pressure (step S801).

The outside temperature refers to the temperature outside the container 10, the inside temperature refers to the temperature inside the container 10, and the humidity refers to the humidity inside the container 10. The gas component value refers to the value of each of the various kinds of components contained in the gas inside the container 10, and the air pressure refers to the air pressure inside the container 10.

In step S802, the internal information acquisition section 202 acquires these pieces of information sequentially outputted from the environmental sensor S2, and sequentially stores thereof in the storage device 105 (refer to FIG. 2).

In addition, though the illustrations are omitted, in the process, the internal information acquisition section 202 also acquires information regarding the set temperature set by the administrator or the like, and also stores the information regarding the set temperature in the storage device 105.

In step S803, the internal information acquisition section 202 generates the index of degradation of the container 10 based on the above-described information stored in the storage device 105.

Specifically, the internal information acquisition section 202 generates, for example, information regarding a heat reflux rate as an index of degradation of the container 10.

Specifically, the internal information acquisition section 202 generates the information regarding the heat reflux rate by use of the following expression (1) every elapse of a predetermined amount of time, $$(\text{cooling capacity of air conditioner 200})/(\text{outside temperature} - \text{inside temperature}) \quad \text{Expression (1)}$$

In addition, the internal information acquisition section 202 finds the change rate in the heat reflux rate based on the heat reflux rate generated at specific timing and the heat reflux rate generated at specific timing prior to the above specific timing.

The internal information acquisition section 202 acquires a new heat reflux rate by use of expression (1) every elapse of a predetermined amount of time, and finds a new change rate.

Then, in step S804, the degradation information generation section 203 determines whether or not the newly obtained change rate exceeds a predetermined threshold (step S804).

In the case where the change rate exceeds the threshold, the degradation information generation section 203 determines that the container 10 is degrading, and sets the degradation establishment flag (step S805).

Note that, similar to the above, in the present embodiment, after the process in step S805, the processes in and after step S801 are performed again. In addition, in the case where it is determined in step S804 that the change rate does not exceed the threshold, the processes in and after step S801 are also performed again.

In the present embodiment, in the case where there is no major change in the state of the container 10, the heat reflux rate is generally constant. When holes or gaps occur in the container 10 due to the degradation of the container 10, the heat reflux rate changes.

In this process example, the degradation of container 10 is grasped by understanding the change in the heat reflux rate.

Note that, to grasp the above-described cooling capacity, the internal information acquisition section 202 grasps the cooling capacity based on information regarding air supplied to the inside of the container 10 by the air conditioner 200 and the information regarding the air conditioner 200.

Specifically, in the case of grasping the cooling capacity based on the information regarding the air, the internal information acquisition section 202 uses the following expression (2) to grasp the cooling capacity.

$$\text{(intake temperature–blow-out temperature)} \times \text{air volume (mass flow rate)} \times \text{specific heat} \quad \text{Expression (2)}$$

Here, the intake temperature refers to the temperature of the gas sucked into the air conditioner 200, and the blow-out temperature refers to the temperature of the gas discharged from the air conditioner 200. In addition, the air volume refers to the amount of gas discharged from the air conditioner 200.

In addition, in the case of grasping the cooling capacity based on the information regarding the air conditioner 200, the internal information acquisition section 202 uses the following expression (3) to grasp the cooling capacity.

$$\text{refrigerant circulation amount (compressor discharge amount (volume)} \times \text{number of revolutions} \times \text{refrigerant density)} \times \text{specific enthalpy difference in refrigerant between inlet and outlet of evaporator} \quad \text{Expression (3)}$$

Note that the refrigerant density is grasped based on, for example, the suction temperature and pressure of a compressor. In addition, the specific enthalpy is grasped based on the suction pressure of a compressor and the temperatures at the inlet and outlet of an evaporator.

Moreover, other than the above, in the process of step S803, the internal information acquisition section 202 generates, for example, information regarding the humidity inside the container 10 as an index of degradation of the container 10.

Specifically, the internal information acquisition section 202 acquires the information regarding the humidity obtained at specific timing and the information regarding the humidity obtained at specific timing prior to the above specific timing from the storage device 105 (refer to FIG. 2).

Then, the internal information acquisition section 202 generates the index of degradation of the container 10 based on the acquired two pieces of information regarding the humidity. Specifically, the internal information acquisition section 202 generates information regarding the change rate in the humidity based on the two pieces of information regarding the humidity.

Then, the degradation information generation section 203 determines, in the next step S804, whether or not the change rate having been generated exceeds a predetermined threshold (step S804).

In the case where the change rate exceeds the predetermined threshold, the degradation information generation section 203 then sets the degradation establishment flag (step S805).

Basically, the humidity inside the container 10 is kept constant, and in the case where the humidity inside the container 10 changes, it is estimated that there are holes or gaps in the container 10.

In the case where the outside temperature is higher than the inside temperature, the humidity inside the container 10 increases when the outside air enters the container 10 from the holes and gaps in the container 10.

In addition, in the case where the outside temperature is lower than the inside temperature, the humidity inside the container 10 decreases if the outside air enters the container 10 from the holes and gaps in the container 10.

In this process example, the degradation of the container 10 is grasped by understanding the change in the humidity inside the container 10.

Moreover, other than the above, in the process of step S803, the internal information acquisition section 202 acquires, for example, information regarding the gas component value inside the container 10 as an index of degradation of the container 10.

Specifically, the internal information acquisition section 202 grasps gas component value at specific timing and the gas component value at specific timing prior to the above specific timing. The internal information acquisition section 202 then acquires the change rate of the component value.

Then, the process proceeds to step S804, and the degradation information generation section 203 determines whether or not the change rate exceeds a predetermined threshold. In the case where the change rate exceeds the predetermined threshold, the degradation information generation section 203 then sets the degradation establishment flag (step S805).

Here, as described above, the container 10 is sometimes provided with a supply device that supplies oxygen or carbon dioxide, and in this case, the gas component value inside the container 10 is kept constant.

In this case, if the component value varies, it is estimated that the holes or gaps occur in the container 10. Then, in the present embodiment, in the case where the change rate exceeds the predetermined threshold, the degradation establishment flag is set.

Moreover, other than the above, in the process of step S803, the internal information acquisition section 202 generates, for example, information regarding the pressure inside the container 10 as an index of degradation of the container 10.

Specifically, the internal information acquisition section 202 grasps the change rate of the pressure based on the pressure inside the container 10 at specific timing and the pressure inside the container 10 at specific timing prior to the above specific timing.

Then, in step S804, the degradation information generation section 203 determines whether or not the grasped change rate exceeds a predetermined threshold.

In the case where the grasped change rate exceeds the predetermined threshold, similar to the above, the degradation information generation section 203 then sets the degradation establishment flag (step S805).

Here, as described above, the container 10 is provided with a supply device that supplies oxygen or carbon dioxide, and the inside of the container 10 is compressed or the air inside the container 10 is discharged to the outside of the container 10 by the supply device.

In this case, the inside of the container 10 is brought into the compressed state or decompressed state.

In this case, if a hole or gap occurs in the container 10, the compressed state or decompressed state cannot be maintained and the pressure inside the container 10 changes. In this process example, the change in the pressure is detected to grasp degradation of the container 10.

Figure 9:
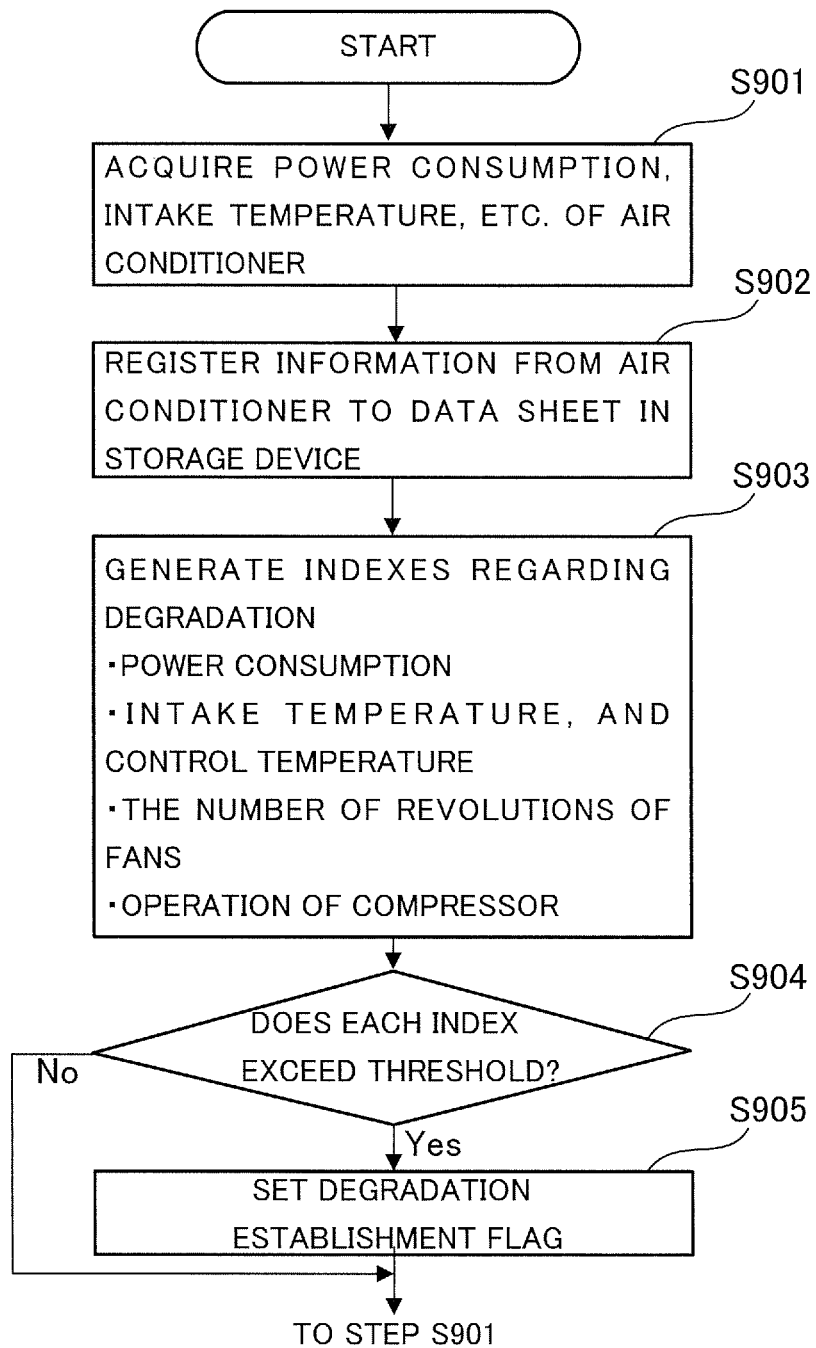
FIG. 9 is a flowchart showing a flow of an acquisition process of an operation status of an air conditioner and a generation process of degradation information based on the operation status of the air conditioner.

FIG. 9 is a flowchart showing a flow of the acquisition process of the operation status of the air conditioner 200 and the generation process of degradation information based on the operation status of the air conditioner 200.

In the process of (C), the internal information acquisition section 202 sequentially acquires information, such as the power consumption, the intake temperature, the set temperature, the control temperature, the number of revolutions of fans, the operating status of the compressor, and the like from the air conditioner 200 (step S901).

Then, every acquisition of these pieces of information from the air conditioner 200, the internal information acquisition section 202 registers these acquired pieces of information, which are associated with one another, to a data sheet stored in the storage device 105 (refer to FIG. 2) (step S902).

Next, the internal information acquisition section 202 generates the index of degradation of the container 10 based on the information registered in the data sheet (step S903).

Specifically, the internal information acquisition section 202 generates, for example, information regarding the difference in the power consumption as an index of degradation of the container 10.

Specifically, first, the internal information acquisition section 202 grasps an estimated power consumption of the air conditioner 200 at specific timing. The internal information acquisition section 202 grasps the estimated power consumption based on, for example, various kinds of pieces of information, such as the initial performance, the outside temperature, the inside temperature, and the cooling capacity of the air conditioner 200.

In addition, the internal information acquisition section 202 acquires the actual power consumption of the air conditioner 200 at the specific timing. The actual power consumption refers to the actual electric power used by the air conditioner 200.

Then, the internal information acquisition section 202 generates a difference between the estimated power consumption and the actual power consumption as the index of degradation of the container 10. Note that, similar to the above, the generation is performed every elapse of a predetermined constant time.

Then, in step S904, the degradation information generation section 203 determines whether or not the difference exceeds a predetermined threshold. In the case where the difference exceeds the predetermined threshold, similar to the above, the degradation information generation section 203 then sets the degradation establishment flag (step S905).

When a hole or gap occurs in the container 10, the actual power consumption increases, and thereby the expected power consumption and the actual power consumption are deviated from each other. In the present embodiment, the degradation of the container 10 is detected by detecting the deviation.

Note that, similar to the above, after the process in step S905, the processes in and after step S901 are performed again. In addition, in the case where it is determined in step S904 that the difference does not exceed the predetermined threshold, the processes in and after step S901 are also performed again.

Moreover, other than the above, in the process in step S903, the internal information acquisition section 202 acquires, for example, information regarding the intake temperature or information regarding the control temperature as an index of degradation of the container 10.

In the case where the internal information acquisition section 202 acquires the information regarding the intake temperature, the internal information acquisition section 202 acquires an estimated value of the intake temperature and an actual measurement value of the intake temperature actually measured.

To acquire the estimated value of the intake temperature, the internal information acquisition section 202 calculates and acquires the estimated value of the intake temperature based on, for example, various kinds of information, such as the outside temperature and the blow-out temperature.

In addition, the internal information acquisition section 202 acquires the actual measurement value based on the output from a not-shown sensor.

Next, the internal information acquisition section 202 obtains a difference between the estimated value and the actual measurement value as the index of degradation of the container 10.

Then, the degradation information generation section 203 carries out the determination process in step S904 to determine whether or not the difference exceeds a predetermined threshold.

In the case where the difference exceeds the predetermined threshold, similar to the above, the degradation information generation section 203 then sets the degradation establishment flag (step S905).

If there are no holes or gaps in the container 10, the above-described estimated value and the above-described actual measurement value are close to each other.

In contrast thereto, if a hole or gap occurs in the container 10, for example, the amount of heat entering the inside of the container 10 from the outside thereof increases; accordingly, the actual measurement value of the intake temperature increases to cause the difference between the estimated value and the actual measurement value to be increased. In the present embodiment, the degradation of the container 10 is grasped based on the difference.

Moreover, in the case where the internal information acquisition section 202 acquires the information regarding the control temperature as the index of degradation of the container 10, the internal information acquisition section 202 acquires the control temperature itself.

In addition, the degradation information generation section 203 acquires the set temperature, which is a temperature preset for the temperature inside the container 10.

Here, the control temperature is the temperature set by a control section (not shown) itself that controls the air conditioner 200, and in the case where the temperature inside the container 10 is higher than the set temperature, the control temperature becomes lower than the set temperature.

The internal information acquisition part 202 obtains the control temperature, the set temperature, and the difference as the index of degradation of the container 10.

Then, the degradation information generation section 203 carries out the determination process in step S904 to determine whether or not the difference exceeds a predetermined threshold.

In the case where the difference exceeds the predetermined threshold, the degradation information generation section 203 then sets the degradation establishment flag (step S905).

In the case where the container 10 has no holes or gaps, in the short term, the state of the container 10 remains balanced, and thereby the control temperature and the set temperature become close to each other.

In contrast thereto, if any hole or gap occurs in the container 10, for example, heat enters the inside of the container 10 from the outside thereof, and the control temperature becomes lower than the set temperature, to thereby generate a difference therebetween.

In this process, the degradation of container 10 is grasped by understanding the difference.

Moreover, other than the above, in the process in step S903, information regarding the number of revolutions of fans installed in the air conditioner 200 may be generated as the index of degradation of the container 10.

In other words, in the process in step S903, information regarding the operation status of the air conditioner 200, which is an example of an appliance that processes the gas inside the container 10, may be generated as the index of degradation of the container 10.

In the case where the information regarding the number of revolutions of fans is generated, the difference between the estimated value of the number of revolutions and the actual number of revolutions is grasped.

Then, the degradation information generation section 203 determines whether or not the difference exceeds the predetermined threshold in step S904, and in the case where the difference exceeds, sets the degradation establishment flag in step S905.

The number of revolutions of fans is affected by the outside temperature, the inside temperature, and the like, and based on these pieces of information, the above-described estimated value regarding the number of revolutions can be obtained.

In addition, if any hole or gap occurs in the container 10, for example, heat enters the inside of the container 10 from the outside thereof, and the fans revolve at the number of revolutions larger than the estimated value.

In this process, the degradation of container 10 is grasped by obtaining the difference between the estimated value and the actual number of revolutions.

Note that, here, the number of revolutions of fans is used; however, other than this, whether or not there is degradation of the container 10 may be determined by obtaining the difference between the estimated operation time of fans and the actual operation time of fans. If any hole or gap occurs in the container 10, heat enters the inside of the container 10 from the outside thereof, and the fans revolve for a time longer than the estimated operation time in some cases.

The degradation of the container 10 can be grasped by obtaining the difference between the estimated operation time and the actual operation time.

Moreover, other than the above, in the process in step S903, information regarding operation of the compressor may be generated as the index of degradation of the container 10.

Specifically, as the index of degradation of the container 10, for example, information regarding the operation time of the compressor is generated. Specifically, similar to the above, the difference between the estimated time regarding the operation time and the actual operation time is obtained to make the difference as the index of degradation of the container 10.

Then, in this case, the degradation information generation section 203 determines in step S904 whether or not the difference exceeds a predetermined threshold.

In the case where the difference exceeds the threshold, similar to the above, the degradation information generation section 203 then sets the degradation establishment flag in step S905.

Here, similar to the above, if any hole or gap occurs in the container 10, for example, heat entering the inside of the container 10 from the outside thereof increases, and the compressor operates for a time longer than the estimated time.

In this process example, the degradation of the container 10 is grasped by obtaining the difference between the estimated time and the actual operation time, which is the operation time in fact.

Note that, here, the description has been given of the case in which the estimated time and the actual operation time are obtained; however, other than this, the estimated number of revolutions (an estimated refrigerant discharge amount) and the actual number of revolutions (an actual refrigerant discharge amount) of the compressor may be obtained. Then, degradation of the container 10 may be grasped based on whether the difference between the estimated number of revolutions and the actual number of revolutions exceeds a predetermined threshold.

Figure 10:
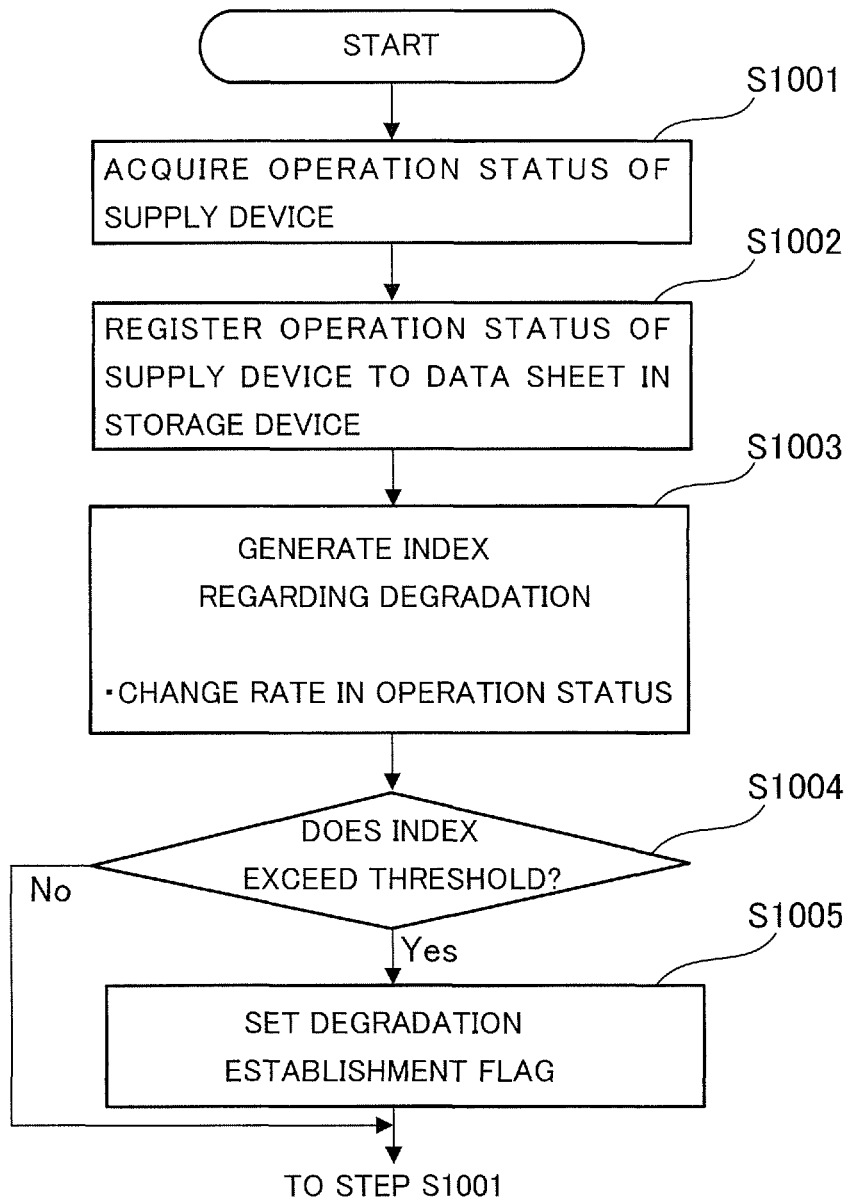
FIG. 10 is a flowchart showing a flow of an acquisition process of an operation status of a supply device and a generation process of degradation information based on the operation status of the supply device.

FIG. 10 is a flowchart showing a flow of the acquisition process of the operation status of the supply device and the generation process of the degradation information based on the operation status of the supply device in the above-described (D).

In this process shown in FIG. 10, the internal information acquisition section 202 acquires the operation status of the supply device from the supply device at a predetermined constant time interval (step S1001).

Specifically, the internal information acquisition section 202 acquires, for example, information regarding the operation time of the supply device per unit time, or the number of revolutions of a pump (an amount of generated gas) as the operation status.

Then, the internal information acquisition section 202 sequentially registers these acquired pieces of information to the data sheet stored in the storage device 105 (refer to FIG. 2) (step S1002).

Here, the supply device can be viewed as an appliance that processes the gas inside the container 10, and in this process example, the information regarding the operation status of the appliance is registered to the data sheet in step S1002.

Then, in the process of step S1003, similar to the above, the internal information acquisition section 202 generates the index of degradation of the container 10.

Specifically, the internal information acquisition section 202 generates a change rate in the operation status of the supply device as the index of degradation of the container 10.

Specifically, the internal information acquisition section 202 finds a change rate between the operation status at specific timing and the operation status at specific timing prior to the above specific timing.

More specifically, the internal information acquisition section 202 finds, for example, a change rate between an operation time per unit time at specific timing and an operation time per unit time at specific timing prior to the above specific timing.

In addition, the internal information acquisition section 202 finds a change rate between the number of revolutions of the pump at specific timing and the number of revolutions of the pump at specific timing prior to the above specific timing.

Then, in step S1004, the degradation information generation section 203 determines whether or not the change rate that has been found exceeds a predetermined threshold.

In the case where the change rate exceeds the predetermined threshold, the degradation information generation section 203 then sets the degradation establishment flag (step S1005).

Note that, here, the description has been given of the case in which the degradation of the container is grasped based on the change rate; however, similar to the above, an estimated value regarding the operation status may be obtained to grasp the degradation of the container based on the difference between the estimated value and the actual measurement value.

After the process in step S1005, similar to the above, the processes in and after step S1001 are performed again. In addition, in the case where it is determined in step S1004 that the change rate does not exceed the predetermined threshold, the processes in and after step S1001 are also performed again.

Figure 11:
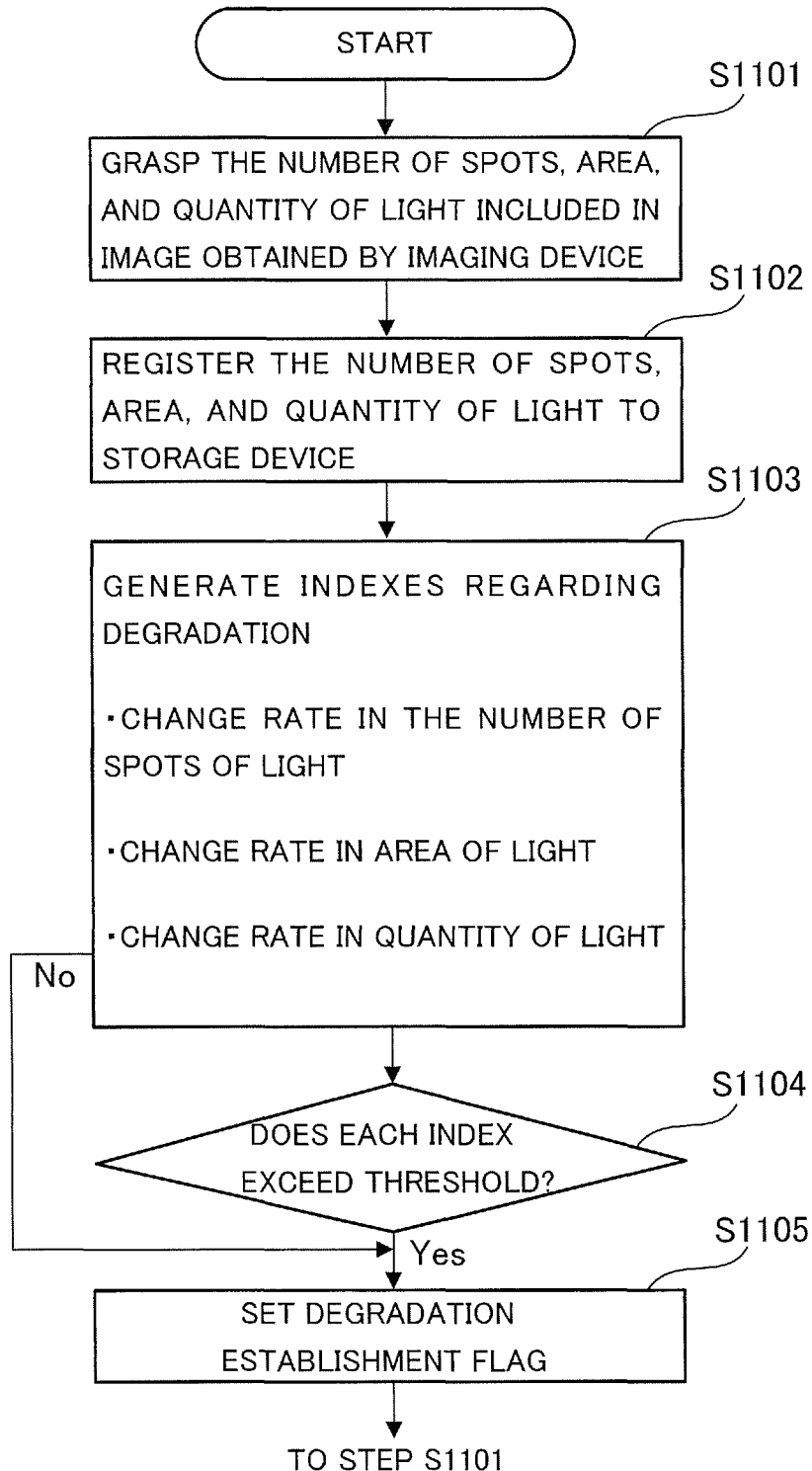
FIG. 11 is a flowchart showing a flow of an acquisition process of an image obtained by an imaging element and a generation process of degradation information based on the image.

FIG. 11 is a flowchart showing a flow of the acquisition process of an image obtained by an imaging device and the generation process of the degradation information based on the image in the above-described (E).

In this process, the internal information acquisition section 202 analyzes the image outputted from the imaging device every elapse of a predetermined constant time, and registers the results of analysis to the storage device 105 (refer to FIG. 2).

Specifically, the internal information acquisition section 202 analyzes the image obtained by the imaging device to grasp the number of spots, area, and quantity of light included in the image (step S1101). Next, the internal information acquisition section 202 associates the number of spots, area, and quantity of light with information indicating the timing, at which these pieces of information were obtained, and then registers thereof to the storage device 105 (step S1102).

The internal information acquisition section 202 performs the processes of these steps S1101 and S1102 every elapse of a predetermined constant time.

When the container 10 degrades and holes or gaps occur in the container 10, the light outside the container 10 enters the inside of the container 10.

In the process of step S1101, information regarding the number of locations where the light enters, the area of the locations where the light enters, and the intensity at the locations where the light enters is acquired.

Then, in step S1102, these pieces of information acquired by the internal information acquisition section 202 are associated with time information, and then registered to the storage device 105.

Thereafter, in this process example, the internal information acquisition section 202 generates the index of degradation of the container 10 based on the information registered to the storage device 105, such as the above-described number of spots, area, and quantity of light (step S1103).

Specifically, the internal information acquisition section 202 finds a change rate in the number of spots based on, for example, the above number of spots obtained at specific timing and the number of spots obtained at specific timing prior to the above specific timing, and regards the change rate as the index of degradation of the container 10.

In addition, the internal information acquisition section 202 finds a change rate in the area based on, for example, the above area obtained at specific timing and the area obtained at specific timing prior to the above specific timing, and regards the change rate as the index of degradation of the container 10.

Moreover, the internal information acquisition section 202 finds a change rate in the quantity of light based on the above quantity of light obtained at specific timing and the quantity of light obtained at specific timing prior to the above specific timing, and regards the change rate as the index of degradation of the container 10.

Then, in step S1104, the degradation information generation section 203 determines whether or not the change rate obtained in step S1103 exceeds a predetermined threshold.

In the case where it is determined that the change rate exceeds the threshold, the degradation information generation section 203 determines that the container 10 is degrading, and sets the degradation establishment flag (step S1105).

Note that the processes in and after step S1105 are similar to the above, and the processes in and after step S1101 are performed again. In addition, in the case where it is determined in step S1104 that the change rate does not exceed the predetermined threshold, the processes in and after step S1101 are also performed again.

Note that it is preferable to install the imaging device to be able to photograph a structurally weak portion of the container 10.

It is preferable to provide the imaging device so that, for example, the location of the container 10 where the door is placed, the corner of the container, the location of the container where there is a seam, and the like can be photographed.

Consequently, when the container degrades, the degradation is more likely to be reflected in the above-described number of spots, area, quantity of light, and the like.

Here, each of the embodiments as described above can be viewed as follows.

(1) An information processing device 100 including: an internal information acquisition section 202 that acquires internal information, which is information regarding inside of a casing 11 containing a fresh item in a refrigerated state or a frozen state; and a degradation information generation section 203 that generates information regarding degradation of the casing 11 based on the internal information acquired by the internal information acquisition section 202.

According to the information processing device 100, the situation of degradation of the casing 11 containing the fresh items can be grasped.

(2) Here, the internal information acquisition section 202 acquires, as the internal information, atmosphere information, which is information regarding an atmosphere inside the casing 11, and the degradation information generation section 203 generates the information regarding the degradation based on the atmosphere information. In this case, the information regarding the degradation of the casing 11 can be generated by obtaining information regarding the atmosphere inside the casing 11.

(3) In addition, the internal information acquisition section 202 acquires, fresh item state information, which is information regarding a state of the fresh items contained in the casing 11, as the internal information, and the degradation information generation section 203 generates the information regarding the degradation based on the fresh item state information. In this case, the information regarding the degradation of the casing 11 can be generated by obtaining information regarding the state of the fresh items contained in the casing 11.

(4) In addition, the internal information acquisition section 202 acquires operation status information, which is information regarding the operation status of the air conditioner 200 that conditions air inside the casing 11, as the internal information, and the degradation information generation section 203 generates the information regarding the degradation based on the operation status information acquired by the internal information acquisition section 202. In this case, the information regarding the degradation of the casing 11 can be generated by obtaining information regarding the operation status of the air conditioner 200 that conditions air inside the casing 11.

(5) In addition, the internal information acquisition section 202 further acquires atmosphere information, which is information regarding an atmosphere inside the casing 11, and the degradation information generation section 203 generates the information regarding the degradation based on the operation status information and the atmosphere information acquired by the internal information acquisition section 202. In this case, the information regarding the degradation of the casing 11 can be generated by obtaining the information regarding the operation status of the air conditioner 200 that conditions air inside the casing 11, and the information regarding the atmosphere inside the casing 11.

(6) In addition, the internal information acquisition section 202 acquires a photographed image obtained by photographing the inside of the casing 11 as the internal information, and the degradation information generation section 203 analyzes the photographed image to generate the information regarding the degradation. In this case, the information regarding the degradation of the casing 11 can be generated by photographing the inside of the casing 11 to obtain the photographed image thereof.

(7) In addition, the degradation information generation section 203 generates the information regarding the degradation based on the internal information acquired by the internal information acquisition section 202 when the casing 11 is in a specific situation. In this case, as compared to the case in which the information regarding the degradation is generated based on the internal information obtained when the casing 11 is not in the specific situation, the accuracy of information, when the information indicating that the casing 11 has degraded is outputted, can be increased.

(8) In addition, the degradation information generation section 203 generates the information regarding the degradation based on the internal information acquired by the internal information acquisition section 202 when another casing 11 is placed on the casing 11. In this case, the information regarding the degradation of the casing 11 can be generated based on the internal information obtained under the situation in which the casing 11 is likely to be deformed.

(9) In addition, the degradation information generation section 203 generates the information regarding the degradation based on the internal information acquired by the internal information acquisition section 202 when the casing 11 is being transported. In this case, the information regarding the degradation of the casing 11 can be generated based on the internal information obtained under the situation in which the casing 11 is likely to be deformed.

(10) In addition, the degradation information generation section 203 generates the information indicating that the casing 11 has degraded in the case where information indicating that a predetermined specific event has occurred more than a predetermined number of times is included in the internal information. In this case, as compared to the case in which the information indicating that the casing 11 has degraded is generated when information indicating that the predetermined specific event has occurred only once is included in the internal information, the accuracy of information, when the information indicating that the casing 11 has degraded is outputted, can be increased.

(11) In addition, the degradation information generation section 203 generates the information regarding the degradation for each of the multiple locations inside the casing 11. In this case, the situation of degradation of the casing 11 can be grasped individually for each of the multiple locations inside the casing 11.

(12) The output section 204, which outputs the information regarding the degradation generated by the degradation information generation section 203 to a predetermined output destination, is further provided. In this case, the generated information regarding the degradation can be outputted to the predetermined output destination.

(13) In addition, the internal information acquisition section 202 acquires information regarding heat reflux rate of the casing 11 as the internal information, and the degradation information generation section 203 generates the information regarding the degradation of the casing 11 based on the change in the heat reflux rate. In this case, the information regarding the degradation of the casing 11 can be generated based on the information regarding the heat reflux rate.

(14) In addition, the internal information acquisition section 202 acquires the operation status of the appliance processing the gas inside the casing 11 as the internal information, and the degradation information generation section 203 generates the information regarding the degradation based on the change in the operation status. In this case, the information regarding the degradation of the casing 11 can be generated based on the operation status of the appliance processing the gas inside the casing 11.

(15) Moreover, a container 10 including: a casing 11 containing a fresh item in a refrigerated state or a frozen state; and an information processing device 100 processing information regarding the casing 11, wherein the information processing device 100 is the information processing device 100 described in any of the above (1) to (14).

According to the container 10, the situation of degradation of the casing 11 containing the fresh item can be grasped.

(16) A program causing a computer to implement: an internal information acquisition function that acquires internal information, which is information regarding inside of a casing 11 containing a fresh item in a refrigerated state or a frozen state; and a degradation information generation function that generates information regarding degradation of the casing 11 based on the internal information acquired by the internal information acquisition function.

According to the program, the status of degradation of the casing 11 containing the fresh item can be grasped.

Each of the above-described configurations is not limited to the above-described embodiments and modified examples thereof, and can be changed within the scope not departing from the spirit. In other words, it can be appreciated that various changes in form and detail may be made without departing from the spirit and scope presently or hereafter claimed.

For example, part of each of the above-described configurations may be omitted, or another function may be added to each of the above-described configurations.

In addition, in the above, multiple embodiments have been described, but the configurations included in one embodiment may be replaced with those included in another embodiment, or the configurations included in one embodiment may be added to another embodiment.

REFERENCE SIGNS LIST

10 Container
11 Casing
100 Information processing device
200 Air conditioner
202 Internal information acquisition section
203 Degradation information generation section
204 Output section

The invention claimed is:

1. An information processing device for monitoring degradation of a casing, the device comprising:
    a processor to execute a program; and
    a memory to store the program which, when executed by the processor, the processor performs processes of:
    acquiring internal information, which is information regarding an inside of the casing containing a fresh item in a refrigerated state or a frozen state, wherein the internal information is fresh item state information which is information regarding a state of the fresh item contained in the casing;
    generating information regarding degradation of the casing based on the acquired internal information; and
    outputting the information regarding the degradation generated by the processor to a predetermined output destination having a display, wherein
    the processor further performs
    generating the information regarding the degradation based on the fresh item state information,
    the display of the predetermined output destination displays the information regarding the degradation to allow an administrator to determine whether a checkup of the casing is encouraged to ensure a proper operation of the casing, and
    the fresh item state information is information that correlates to a quality of the casing.

2. The information processing device according to claim 1, wherein the processor further performs processes of:
    acquiring information regarding a gas that increases or decreases in the casing along with a change in the state of the fresh item contained in the casing, as the fresh item state information, and
    generating the information regarding the degradation based on the information regarding the gas that increases or decreases along with the change in the state of the fresh item.

3. The information processing device according to claim 2, wherein the processor further performs processes of:
    acquiring concentration information, which is information regarding a concentration of a specific gas that increases or decreases along with the change in the state of the fresh item to result in a change in the concentration, as the fresh item state information, and
    generating the information regarding the degradation based on a change rate of the concentration identified by the concentration information.

4. The information processing device according to claim 2, wherein the processor further performs processes of:
    acquiring the information regarding the gas that increases or decreases for each of multiple locations inside the casing, and
    generating the information regarding the degradation for each of the multiple locations inside the casing.

5. The information processing device according to claim 1, wherein the processor further performs a process of generating the information regarding the degradation based on the fresh item state information, which is information regarding the fresh item acquired by the processor, and information regarding an elapsed time since the fresh item was contained in the casing.

6. The information processing device according to claim 1, wherein the processor further performs processes of:
    acquiring fluorescence property information, which is information regarding a fluorescence property of the fresh item, as the fresh item state information, and
    generating the information regarding the degradation based on a change rate of the fluorescence property identified by the fluorescence property information.

7. The information processing device according to claim 1, wherein the processor further performs a process of generating the information regarding the degradation based on the fresh item state information acquired by the processor when the casing is in a specific situation.

8. The information processing device according to claim 7, wherein the processor further performs a process of generating the information regarding the degradation based on the fresh item state information acquired by the processor when another casing is placed on the casing.

9. The information processing device according to claim 7, wherein the processor further performs a process of generating the information regarding the degradation based on the fresh item state information acquired by the processor when the casing is being transported.

10. The information processing device according to claim 1, wherein the processor further performs a process of generating the information indicating that the casing has degraded when the fresh item state information includes information indicating that a predetermined specific event has occurred more than a predetermined number of times.

11. The information processing device according to claim 1, wherein the processor further performs a process of generating the information regarding the degradation for each of multiple locations inside the casing.

12. A storage container comprising:
    a casing containing a fresh item in a refrigerated state or a frozen state; and
    an information processing device processing information regarding the casing, wherein
    the information processing device is the information processing device according to claim 1.

13. A non-transitory computer readable medium storing a program to monitor degradation of a casing and causing a computer to implement:
    an internal information acquisition function acquiring internal information, which is information regarding an inside of the casing containing a fresh item in a refrigerated state or a frozen state, wherein the internal information is fresh item state information which is information regarding a state of the fresh item contained in the casing;

a degradation information generation function generating information regarding degradation of the casing based on the internal information acquired by the internal information acquisition function; and an output function outputting the information regarding the degradation of the casing to a predetermined output destination having a display, wherein the degradation information generation function generates the information regarding the degradation based on the fresh item state information, the output function enables the display of the predetermined output destination to display the information regarding the degradation to allow an administrator to determine whether a checkup of the casing is encouraged to ensure a proper operation of the casing, and the fresh item state information is information that correlates to a quality of the casing.

* * * * *